(12) United States Patent
Saito et al.

(10) Patent No.: US 9,157,922 B2
(45) Date of Patent: Oct. 13, 2015

(54) DISPENSING METHOD

(71) Applicant: Seiko Epson Corporation, Tokyo (JP)

(72) Inventors: Yuji Saito, Shiojiri (JP); Fumio Takagi, Chino (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 14/330,548

(22) Filed: Jul. 14, 2014

(65) Prior Publication Data

US 2014/0322101 A1 Oct. 30, 2014

Related U.S. Application Data

(62) Division of application No. 13/523,100, filed on Jun. 14, 2012, now Pat. No. 8,809,070.

(30) Foreign Application Priority Data

Jun. 22, 2011 (JP) ................. 2011-138674

(51) Int. Cl.
| | | |
|---|---|---|
| *B01L 3/02* | (2006.01) | |
| *G01N 35/10* | (2006.01) | |
| *G01N 1/10* | (2006.01) | |
| *G01N 1/14* | (2006.01) | |
| *G01N 1/38* | (2006.01) | |
| *B01L 7/00* | (2006.01) | |

(52) U.S. Cl.
CPC ............ *G01N 35/1002* (2013.01); *G01N 1/10* (2013.01); *G01N 1/14* (2013.01); *G01N 1/38* (2013.01); *G01N 35/1016* (2013.01); *B01L 3/0241* (2013.01); *B01L 7/52* (2013.01); *B01L 2300/0838* (2013.01); *B01L 2400/049* (2013.01); *B01L 2400/0457* (2013.01); *Y10T 436/118339* (2015.01); *Y10T 436/119163* (2015.01); *Y10T 436/25* (2015.01); *Y10T 436/2575* (2015.01)

(58) Field of Classification Search
CPC ............ G01N 1/10; G01N 1/02; G01N 1/14; G01N 1/18; G01N 1/38; G01N 2001/38; G01N 2001/383; B01L 3/02; B01L 3/0234; B01L 7/52
USPC .......... 436/53–54, 174, 180; 422/82, 93, 501, 422/509, 514–515, 518, 521
See application file for complete search history.

(56) References Cited

U.S. PATENT DOCUMENTS

| | | |
|---|---|---|
| 5,452,619 A | 9/1995 | Kawanabe et al. |
| 5,906,947 A | 5/1999 | Bienhaus et al. |
| 6,709,872 B1 | 3/2004 | Downs et al. |

(Continued)

FOREIGN PATENT DOCUMENTS

| | | |
|---|---|---|
| EP | 1905513 A1 | 4/2008 |
| GB | 2 453 585 A | 4/2009 |

(Continued)

OTHER PUBLICATIONS

Extended European Search Report for Application No. EP 12 17 2724 dated Jan. 18, 2013 (6 pages).

*Primary Examiner* — Brian R Gordon
(74) *Attorney, Agent, or Firm* — Harness, Dickey & Pierce, P.L.C.

(57) ABSTRACT

A dispensing method which dispenses a first liquid contained in a first vessel which stores the first liquid and a second liquid to introduce the first liquid into a second vessel by using a tube.

9 Claims, 6 Drawing Sheets

(56) References Cited

U.S. PATENT DOCUMENTS

| | | |
|---|---|---|
| 6,794,193 B2 | 9/2004 | Fujimoto |
| 8,221,702 B2 * | 7/2012 | Shimoda et al. ............. 422/527 |
| 8,277,756 B2 | 10/2012 | Gorka |
| 8,333,936 B2 | 12/2012 | Miyashita et al. |
| 8,361,807 B2 * | 1/2013 | Wiyatno et al. ............. 436/180 |
| 8,465,707 B2 | 6/2013 | Curran et al. |
| 8,580,198 B2 | 11/2013 | Onuma |
| 2003/0073110 A1 | 4/2003 | Aritomi et al. |
| 2003/0213905 A1 * | 11/2003 | Lennon et al. ............. 250/288 |
| 2005/0282291 A1 * | 12/2005 | Pankratz et al. ............. 436/180 |
| 2006/0110831 A1 | 5/2006 | Kijlstra et al. |
| 2010/0304443 A1 | 12/2010 | Davies et al. |

FOREIGN PATENT DOCUMENTS

| | | |
|---|---|---|
| JP | 2000-304754 A | 11/2000 |
| JP | 2004-025148 A | 1/2004 |
| JP | 2007-074960 A | 3/2007 |
| JP | 2007-175002 A | 7/2007 |
| JP | 2009-097939 A | 5/2009 |

* cited by examiner

DISPENSING METHOD

CROSS-REFERENCE TO RELATED APPLICATIONS

This is a divisional patent application of U.S. application Ser. No. 13/523,100, now U.S. Pat. No. 8,809,070 filed Jun. 14, 2012, which claims priority to Japanese Patent Application No. 2011-138674, filed Jun. 22, 2011, all of which are hereby incorporated by reference in their entireties.

BACKGROUND

1. Technical Field

The present invention relates to a dispensing method.

2. Related Art

PCR (polymerase chain reaction) is an established technology in the biochemical field. With recent improvement over amplification accuracy and detection sensitivity in the PCR method, even an extremely small amount of a specimen (such as DNA) has been amplified, detected, and analyzed.

It is preferable that the PCR method uses only a small amount (volume) of a reaction liquid in view of cost and efficiency, considering the fact that the specimen and reagent employed for the PCR method are often rare and expensive. Therefore, such a technique which only requires the smallest possible amount of a reaction liquid for the PCR method has been demanded. JP-A-2004-025148 discloses a method for handling a small amount of liquid, for example. According to this method, a target liquid is sent through a narrow tube with the aid of a sending liquid not miscible with the target liquid but separable in phase therefrom. Moreover, JP-A-2007-175002 proposes a gene analyzing device which performs PCR by shifting a PCR reaction liquid within a channel, and a method for using this device. According to the techniques disclosed in these references, the volume of the target liquid to be handled is larger than 0.5 µL (microliter), wherefore the target liquid has been otherwise prepared separately on a larger scale. For preparation of the target liquid, therefore, an instrument or an experimental tool available on the market has been used, for example. However, particularly for PCR recently developed, preparation of the target liquid of a volume around 1 µL has been required with improvement over micro-reaction technologies and the increasing demand for cost reduction. For meeting this requirement, an accurate volume of solution containing specimens and reagents in nanoliters (less than 1 µL) needs to be measured, sent, and handled in various ways. However, the dispensing method used in the techniques of the above references or the like is difficult to handle this volume of liquid with sufficient accuracy. Even when a manually operated pipet, which is regarded as a relatively accurate tool, is used for preparation of the target liquid, for example, a volume of liquid as small as less than 0.2 µL is difficult to be measured, sent, and dispensed with sufficient accuracy.

Moreover, liquid of an amount as small as on the scale of microliters or nanoliters (less than 100 µL) partially evaporates in some cases during measurement, dispensation or other processes. In this case, the amount of the liquid or the concentration of the solutes changes.

SUMMARY

An advantage of some aspects of the invention is to provide a dispending method which can dispense a small amount of liquid with high accuracy.

Application Example 1

This application example of the invention is directed to a dispensing method which dispenses a first liquid contained in a first vessel which stores the first liquid and a second liquid not miscible with the first liquid and having lower specific gravity than that of the first liquid so as to introduce the first liquid into a second vessel by using a tube. The method includes: a first suction step which sucks the second liquid to introduce this second liquid into the tube through one end of the tube; a second suction step which sucks the first liquid contained in the first vessel to introduce this first liquid into the tube through the one end of the tube; a third suction step which sucks the second liquid contained in the first vessel to introduce this second liquid into the tube through the one end of the tube; a first discharge step which releases the second liquid sucked into the tube in the third suction step to discharge this second liquid into the second vessel; a second discharge step which releases the first liquid sucked into the tube in the second suction step to discharge this first liquid into the second liquid contained in the second vessel; and a third discharge step which releases at least a part of the second liquid sucked into the tube in the first suction step to discharge this second liquid into the second vessel.

According to the dispensing method of this application example, the first liquid contained in the first vessel and during the respective suction steps and discharge steps is sealed by the second liquid, and therefore is difficult to contact a gaseous phase (such as air). In other words, according to the dispensing method of this application example, the first liquid is handled in the condition of contact with the second liquid during dispensation from the first vessel to the second vessel, and therefore is difficult to contact the air and the like. In this case, evaporation of the constituent components of the first liquid into a gaseous phase, and entrance of other substances such as water through a gaseous phase into the first liquid can be prevented. Accordingly, variations in the concentrations of the solvent and solutes of the first liquid decrease, which contributes to accurate dispensation.

Moreover, according to the dispensing method of this application example, the first liquid is discharged into the second liquid in the second discharge step. In this case, the first liquid is difficult to remain within the tube or in the vicinity of the one end of the tube in the second discharge step. Accordingly, the first liquid contained in the first vessel can be accurately dispensed into the second vessel.

In this specification, dispensation refers to division of a predetermined amount of a liquid from a vessel containing this liquid and shift of the divided liquid into another vessel. As will be easily understood by those skilled in the biochemical field, the term expressing this operation corresponds to "dispensation" in English. An instrument used for dispensation is called a "dispenser" or the like in English. The dispensing method according to the invention is not limited to a method used in the biochemical field but is applicable to a method used in a variety of fields such as chemical, pharmaceutical, biological, and engineering fields. Moreover, "to dispense" in this specification includes both the operation of extracting a liquid from a predetermined vessel and introducing at least a part of this liquid into another vessel, and the operation of extracting a liquid from a predetermined vessel and introducing a predetermined amount of this liquid into each of plural other vessels.

In this specification, the tube corresponds to a tube-shaped component which has an inside diameter so sized as to maintain a plug shape of the first liquid within the tube. The liquid forming the plug shape occupies substantially the entire inner space of a part of the tube in the longitudinal direction of the tube in such a manner as to divide another substance contained in the tube. The term "substantially" herein includes a condition in which a thin film of another substance (such as second liquid) exists on the inner wall of the tube, for example.

Application Example 2

This application example of the invention is directed to a dispensing method which dispenses a first liquid contained in a first vessel which stores the first liquid and a second liquid not miscible with the first liquid and having lower specific gravity than that of the first liquid, and a third liquid not miscible with the second liquid and having higher specific gravity than that of the second liquid and contained in a third vessel which stores the second liquid and the third liquid to as to introduce the first liquid and the third liquid into a second vessel by using a tube. The method includes: a first suction step which sucks the second liquid to introduce this second liquid into the tube through one end of the tube; a second suction step which sucks the first liquid contained in the first vessel to introduce this first liquid into the tube through the one end of the tube; a third suction step which sucks the second liquid contained in the first vessel to introduce this second liquid into the tube through the one end of the tube; a fourth suction step which sucks the third liquid contained in the third vessel to introduce this third liquid into the tube through the one end of the tube; a fifth suction step which sucks the second liquid contained in the third vessel to introduce this second liquid into the tube through the one end of the tube; a first discharge step which releases the second liquid sucked into the tube in the fifth suction step to discharge this second liquid into the second vessel; a second discharge step which releases the third liquid sucked into the tube in the fourth suction step to discharge this third liquid into the second vessel; a third discharge step which releases apart of the second liquid sucked into the tube in the third suction step to discharge this second liquid into the second vessel; a fourth discharge step which releases the second liquid remaining within the tube after the third discharge step to discharge this second liquid into the second vessel; a fifth discharge step which releases the first liquid sucked into the tube in the second suction step to discharge this first liquid into the second vessel; and a sixth discharge step which releases at least a part of the second liquid sucked into the tube in the first suction step to discharge this second liquid into the second vessel.

According to the dispensing method of this application example, the first liquid and the third liquid shifted from the first vessel and the third vessel and introduced into the second vessel and during the respective suction steps and discharge steps are sealed by the second liquid. Therefore, the first liquid and the third liquid are difficult to contact a gaseous phase (such as air). In other words, during dispensation by the dispensing method of this application example, the first liquid and the third liquid are handled in the condition of contact with the second liquid and therefore difficult to contact the air and the like. In this case, evaporation of the constituent components of the first liquid and the third liquid into a gaseous phase, and entrance of other substances such as water through a gaseous phase into the first liquid or the third liquid can be prevented. Accordingly, variations in the concentrations of the first liquid and the third liquid decrease, which contributes to accurate dispensation.

Moreover, according to the dispensing method of this application example, the third liquid is discharged into the second liquid in the fifth discharge step, and the first liquid is discharged into the second liquid in the second discharge step. In this case, the third liquid and the first liquid are difficult to remain within the tube or in the vicinity of the one end of the tube during the fifth discharge step and the second discharge step. Accordingly, the first liquid and the third liquid can be accurately dispensed into the second vessel.

Application Example 3

This application example of the invention is directed to a dispensing method which dispenses a first liquid contained in a first vessel which stores the first liquid and a second liquid not miscible with the first liquid and having lower specific gravity than that of the first liquid, and a third liquid not miscible with the second liquid and having higher specific gravity than that of the second liquid and contained in a third vessel which stores the second liquid and the third liquid so as to introduce the first liquid and the third liquid into a second vessel by using a tube one end of which is opened and the other end of which is connected with a reservoir. The method includes: a first suction step which sucks the second liquid to introduce this second liquid into the tube through the one end of the tube; a second suction step which sucks the first liquid contained in the first vessel to introduce this first liquid into the tube through the one end of the tube; a third suction step which sucks the second liquid contained in the first vessel to introduce this second liquid into the tube through the one end of the tube; a fourth suction step which sucks the third liquid contained in the third vessel to introduce this third liquid into the tube through the one end of the tube; a fifth suction step which sucks the second liquid contained in the third vessel to introduce this second liquid into the tube through the one end of the tube; a mixing step which sucks the respective liquids contained in the tube to introduce these liquids into the reservoir such that at least a part of the second liquid sucked in the fifth suction step remains within the tube, mixes the first liquid sucked into the tube in the second suction step and the third liquid sucked into the tube in the fourth suction step to produce a fourth liquid mixed in the reservoir, and mixes the second liquids sucked in the first suction step, the third suction step, and the fifth suction step; a first discharge step which releases the second liquid remaining within the tube to discharge this second liquid into the second vessel; a second discharge step which releases the fourth liquid to discharge this fourth liquid into the second vessel; and a third discharge step which releases at least a part of the second liquid mixed in the mixing step to discharge this second liquid into the second vessel.

According to the dispensing method of this application example, the first liquid and the third liquid can be securely mixed with each other. More specifically, according to the dispensing method of this application example, the liquid drops of the first liquid and the third liquid are combined into a liquid drop of the fourth liquid within the reservoir by the mixing step. In this case, the first liquid and the third liquid can be more easily brought into contact with each other than in such a case where the liquid drops of the first liquid and the third liquid are combined within the second vessel after separately discharged into the second vessel. Accordingly, more reliable mixture of the first liquid and the third liquid can be achieved by the dispensing method of this application example.

Moreover, according to the dispensing method of this application example, the first liquid, the third liquid, and the fourth liquid shifted from the first vessel and the third vessel and introduced into the second vessel and during the respective suction steps, mixing step and discharge steps are sealed by the second liquid. Therefore, the first liquid, the third liquid, and the fourth liquid are difficult to contact a gaseous phase (such as air). In other words, during dispensation by the dispensing method of this application example, the first liquid, the third liquid, and the fourth liquid are handled in the condition of contact with the second liquid and therefore difficult to contact the air and the like. In this case, evaporation of the constituent components of the first liquid, the third liquid, or the fourth liquid into a gaseous phase, and entrance of other substances such as water through a gaseous phase into the first liquid, the third liquid, or the fourth liquid can be prevented. Accordingly, variations in the concentrations of the first liquid, the third liquid, and the fourth liquid decrease, which contributes to accurate dispensation.

Furthermore, according to the dispensing method of this application example, the fourth liquid is discharged into the second liquid in the second discharge step. In this case, the fourth liquid is difficult to remain within the tube or in the vicinity of the one end of the tube during the second discharge step. Accordingly, the fourth liquid can be accurately dispensed into the second vessel.

Application Example 4

In the dispensing method according to any of Application Examples 1 to 3, the second liquid may be contained in the second vessel beforehand.

According to the dispensing method of this configuration, the one end of the tube can be easily brought into contact with the second liquid during the respective discharge steps. In this case, the first liquid, the third liquid, or the fourth liquid is more difficult to remain within the tube or in the vicinity of the one end of the tube. Accordingly, the first liquid, the third liquid, or the fourth liquid can be further accurately dispensed into the second vessel.

Application Example 5

This application example of the invention is directed to a dispensing method which dispenses a first liquid contained in a first vessel which stores the first liquid and a second liquid not miscible with the first liquid and having lower specific gravity than that of the first liquid so as to introduce the first liquid into a second vessel by using a tube, which second vessel stores a third liquid not miscible with the first liquid and miscible with the second liquid. The method includes: a first suction step which sucks the second liquid or the third liquid to introduce this second or third liquid into the tube through one end of the tube; a second suction step which sucks the first liquid contained in the first vessel to introduce this first liquid into the tube through the one end of the tube; a third suction step which sucks the second liquid contained in the first vessel to introduce this second liquid into the tube through the one end of the tube; a first discharge step which releases the second liquid sucked into the tube in the third suction step to discharge this second liquid into the second vessel; a second discharge step which releases the first liquid sucked into the tube in the second suction step to discharge this first liquid into the second vessel; and an eleventh discharge step which releases at least apart of the second liquid or the third liquid sucked into the tube in the first suction step to discharge this second or third liquid into the second vessel.

According to the dispensing method of this application example, the first liquid shifted from the first vessel and introduced into the second vessel and during the respective suction steps and discharge steps is sealed by the second liquid or the third liquid, and therefore is difficult to contact a gaseous phase (such as air). In other words, according to the dispensing method of this application example, the first liquid is handled in the condition of contact with the second liquid or the third liquid during shift of the first liquid from the first vessel to the second vessel for dispensation, and therefore is difficult to contact the air and the like. In this case, evaporation of the constituent components of the first liquid into a gaseous phase, and entrance of other substances such as water through a gaseous phase into the first liquid can be prevented. Accordingly, variations in the concentrations of the solvent and solutes of the first liquid decrease, which contributes to accurate dispensation.

Moreover, according to the dispensing method of this application example, the first liquid is discharged into the mixture of the third liquid and the second liquid in the second discharge step. In this case, the first liquid is difficult to remain within the tube or in the vicinity of the one end of the tube during the second discharge step. Accordingly, the first liquid contained in the first vessel can be accurately dispensed into the second vessel.

Application Example 6

In the dispensing method according to Application Example 5, the third liquid may have conductivity.

According to the dispensing method of this configuration, conductivity given to the third liquid can prevent an unexpected action of either the first liquid or the second liquid when at least either the first liquid or the second liquid is charged, which action may be caused through the electrostatic attractive force or repulsive force produced between the third liquid and the charged first liquid or second liquid in the vicinity of the tip of the tube during the respective discharge steps. Accordingly, the first liquid contained in the first vessel can be more securely dispensed into the second vessel.

Application Example 7

In the dispensing method according to any of Application Examples 1 to 6, the second liquid may have conductivity.

According to the dispensing method of this configuration, conductivity given to the second liquid can prevent an unexpected action of at least the first liquid when the respective liquids are charged, which action may be caused through the electrostatic attractive force or repulsive force produced between the first liquid and the second vessel or substances contained in the second vessel in the vicinity of the tip of the tube during the respective discharge steps. Accordingly, the first liquid can be more securely dispensed into the second vessel.

Application Example 8

In the dispensing method according to any of Application Examples 1 to 7, at least the inner wall of the tube may have hydrophobic property.

According to the dispensing method of this configuration, water-base liquid does not easily adhere to the inner wall of the tube. Thus, when the first liquid, the third liquid, and the fourth liquid are water solutions, the first liquid, the third liquid, and the fourth liquid can more smoothly shift within the tube during the second suction step and the subsequent respective steps. Moreover, the first liquid, the third liquid, and the fourth liquid are more difficult to remain within the tube in the respective discharge steps. Accordingly, more accurate dispensation of the liquids can be achieved.

BRIEF DESCRIPTION OF THE DRAWINGS

The invention will be described with reference to the accompanying drawings, wherein like numbers reference like elements.

DESCRIPTION OF EXEMPLARY EMBODIMENTS

Exemplary embodiments according to the invention are hereinafter described. The respective embodiments shown herein are only examples of the invention, and therefore the scope of the invention is not limited to these embodiments but includes various modifications made thereto without departing from the scope of the invention. All the structures and steps shown in the following embodiments are not necessarily the essential elements for practicing the invention.

1. First Embodiment

Figure 1:
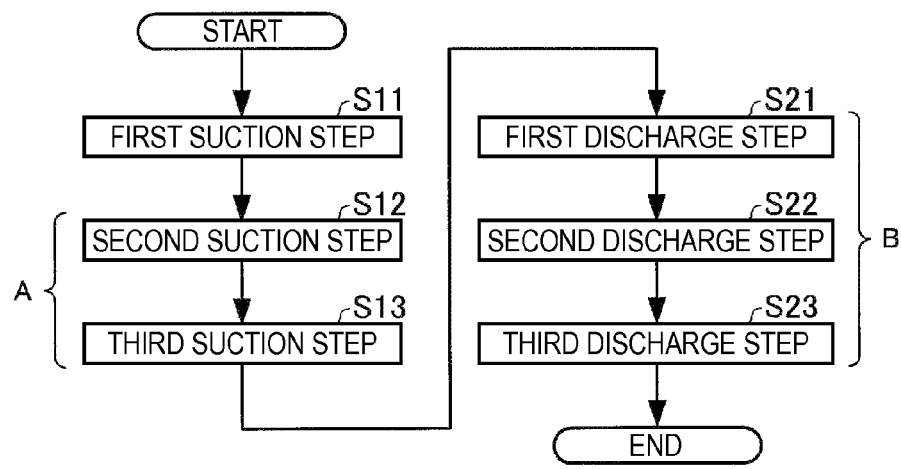
FIG. 1 is a flowchart showing the flow of a dispensing method according to a first embodiment.
Figures 2A, 2B, 2C, 2D:
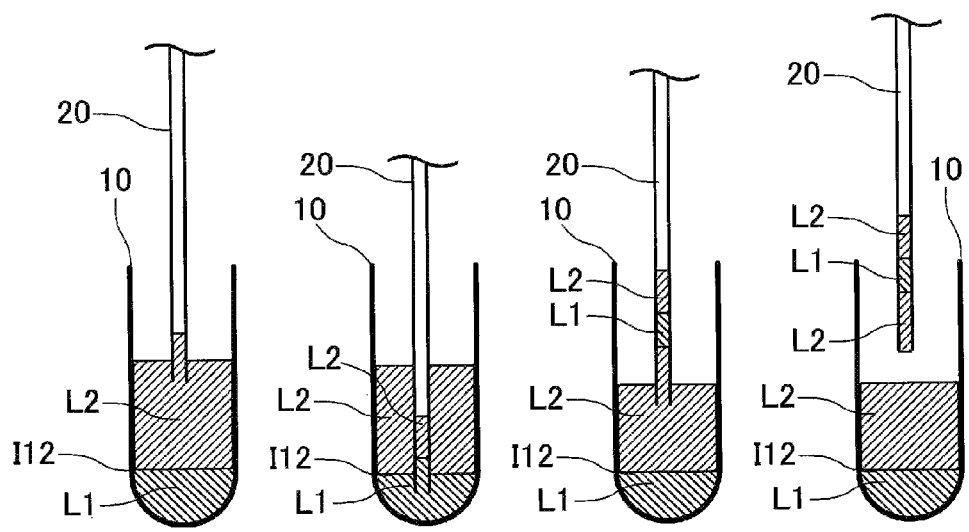
FIG. 2A schematically illustrates a first suction step according to the first embodiment.
FIG. 2B schematically illustrates a second suction step according to the first embodiment.
FIG. 2C schematically illustrates a third suction step according to the first embodiment.
FIG. 2D schematically illustrates a condition after the third suction step according to the first embodiment.
Figures 3A, 3B, 3C, 3D:
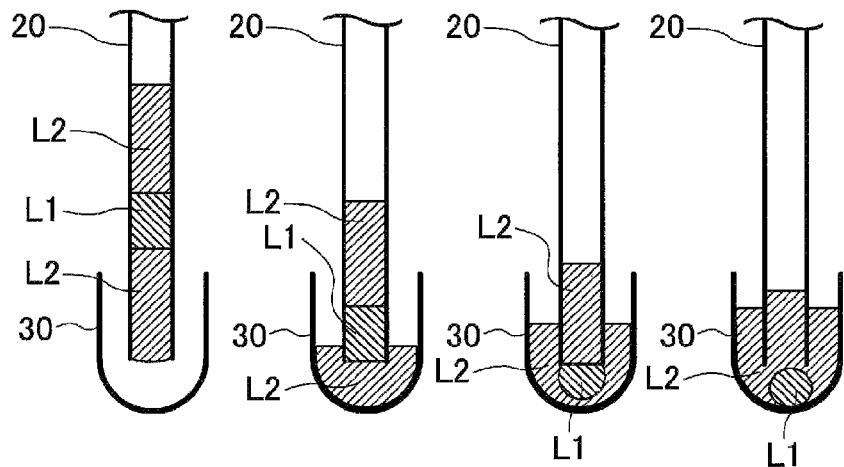
FIG. 3A schematically illustrates a preparatory condition before a first discharge step according to the first embodiment.
FIG. 3B schematically illustrates the first discharge step according to the first embodiment.
FIG. 3C schematically illustrates a second discharge step according to the first embodiment.
FIG. 3D schematically illustrates a third discharge step according to the first embodiment.

A dispensing method according to a first embodiment of the invention is hereinafter described. FIG. 1 is a flowchart showing the flow of the dispensing method in this embodiment. Each of FIGS. 2A through 2D and FIGS. 3A through 3D schematically illustrates a part of the steps performed in the dispensing method according to this embodiment. FIG. 2A schematically illustrates a first suction step in this embodiment. FIG. 2B schematically illustrates a second suction step in this embodiment. FIG. 2C schematically illustrates a third suction step in this embodiment. FIG. 2D schematically illustrates a condition after the third suction step in this embodiment. FIG. 3A schematically illustrates a preparatory condition before a first discharge step in this embodiment. FIG. 3B schematically illustrates the first discharge step in this embodiment. FIG. 3C schematically illustrates a second discharge step in this embodiment. FIG. 3D schematically illustrates a third discharge step in this embodiment.

1.1. Structure

The dispensing method according to this embodiment is a method for dispensing a first liquid L1 contained in a first vessel 10 which stores the first liquid L1 and a second liquid L2 to introduce the first liquid L1 into a second vessel 30 via a tube 20.

1.1.1. First Liquid

The first liquid L1 is a liquid not miscible with the second liquid L2 described later. In addition, the first liquid L1 is a liquid having higher specific gravity than that of the second liquid L2. When the first liquid L1 having these characteristics is used, an interface I12 is produced between the first liquid L1 and the second liquid L2 coexisting within the first vessel 10 as illustrated in FIGS. 2A through 2D. In other words, the first liquid L1 and the second liquid L2 are in a liquid-liquid phase-separated condition when coexisting. In this case, the first liquid L1 is positioned on the lower side of the interface I12 in the direction of gravity (bottom side of the first vessel 10), while the second liquid L2 is positioned on the upper side of the interface I12 (opening side of the first vessel 10). The first liquid L1 has surface tension, and forms a liquid drop within the second liquid L2 when the volume of the first liquid L1 is sufficiently small. In this specification, the terms "upper side" and "lower side" refer to the upper side and the lower side with respect to the direction of gravity. The first liquid L1 may be either of water-base type or of oil-base type. When the first liquid L1 is a water-base type liquid, for example, the second liquid L2 may be of oil-base type. Conversely, the first liquid L1 and the second liquid L2 may be an oil-base type liquid and a water-base type liquid, respectively.

The first liquid L1 may be a reaction liquid used for PCR (polymerase chain reaction), or a solution used for preparing a reaction liquid for PCR. When the first liquid L1 is a reaction liquid for PCR, this reaction liquid contains nucleic acids (target nucleic acids) as an amplification target, and reagents necessary for causing reaction (such as DNA polymerases and primers). When the first liquid L1 is a solution used for preparing a reaction liquid for PCR, the first liquid L1 may be a solution containing nucleic acids (target nucleic acids) or at least one type of reagents necessary for causing reaction. In this case (or in other cases), apart of the remaining reagents may be contained in the second vessel 30 beforehand. Moreover, the first liquid L1 may be a solution containing substances easily oxidized by oxygen contained in the atmosphere, or substances easily reacting to molecules such as those of water contained in the atmosphere.

1.1.2. Second Liquid

The second liquid L2 is a liquid not miscible with the first liquid L1. In addition, the second liquid L2 is a liquid having lower specific gravity than that of the first liquid L1. The second liquid L2 may be a liquid of oil-base type when the first liquid L1 is of water-base type. For example, when the first liquid L1 is a reaction liquid for PCR, or a solution used for preparing a reaction liquid for PCR, the second liquid L2 may be formed by oil. Examples of oil used as the material of the second liquid L2 include oils of the silicon family such as dimethyl silicon oil, oils of the paraffin family, mineral oil, and a mixture of these oils.

1.1.3. Tube

The tube 20 has openings at both ends thereof, and contains a channel which connects these openings to allow communication therebetween and flow of liquid through the channel. In this specification, an end of the tube 20 on one side is referred to as "one end", while an end of the tube 20 on the other side is referred to as "the other end".

The inside diameter of the tube 20 corresponds to the maximum diameter of the tube 20 on the cross section of the channel of the tube 20. The shape of the tube 20 may be arbitrarily determined. For example, the tube 20 may have a cylindrical shape. The length and the inside diameter of the tube 20 may be arbitrarily determined as long as the first liquid L1 can form a plug within the tube 20. The tube 20 may be either linear or bended in a certain shape. When liquids to be handled such as the first liquid L1 and the second liquid L2 are reaction liquids for PCR or the like, it is preferable that the inside diameter of the tube 20 is 0.2 mm or shorter. When the inside diameter of the tube 20 is 0.2 mm, a 1 mm-long liquid column formed therein has a volume of approximately 30 nanoliters (nL).

The inside diameter of the tube 20 is so sized as to maintain a plug shape of the first liquid L1 within the tube 20.

The first liquid L1 forming the plug shape occupies substantially the entire inner space of a part of the tube 20 in the longitudinal direction (direction along the channel) in such a manner as to separate another substance contained in the tube 20 in the longitudinal direction of the tube 20. This condition of the tube 20 includes such a condition in which another thin-film-shaped substance (such as second liquid) exists on the inner wall of the tube 20, for example.

A specific example of the tube 20 is a capillary tube (capillary) both ends of which are opened. The tube 20 introduces liquid or gas from the one end into the channel by suction (depressurization) of the interior of the channel from the other end. The method for sucking the interior of the channel from the other end of the tube 20 is not specifically limited but may be arbitrarily determined, such as a method using a pump, a pipetter, or a syringe, for example, or may be sucked through the mouth of an operator. Moreover, the tube 20 can discharge liquid or gas from the one end by pressurization of the inside of the channel from the other end. In this specification, the end of the tube 20 to which a device for pressurization or depressurization is attached corresponds to the other end, while the end of the tube 20 through which liquid is sucked or discharged corresponds to the one end. Since a plug of liquid is formed within the tube 20 in suction steps described later, liquid is discharged in the order opposite to the order of suction (so-called "first-in last-out"). The method for pressurizing the interior of the channel from the other end of the tube 20 is not specifically limited but may be arbitrarily determined, such as a method using a pump, a pipetter, or a syringe having sucking and pressurizing function, for example, or may be pressurized by breath introduced from the mouth of an operator. When the first liquid L1 of a volume of 1 microliter (μL) or smaller is sucked or discharged, it is preferable that the flow speed within the tube 20 is 1 μL/s or lower, more preferably 1 μL/minute or lower. In this case, it is preferable that the device such as a pump and a pipetter used for suction and discharge can produce flow of liquid at a speed in this range.

The tube 20 may be made of inorganic material (such as heat-resisting glass (Pyrex (registered trademark))), organic material (such as polycarbonate, polypropylene, PTFE (polytetrafluoroethylene) and other resin), for example, or a composite of these materials.

It is preferable that the tube 20 is made of material which transmits visible light such as glass and polycarbonate to allow visual observation of the (phase-separation) interface I12 formed between the first liquid L1 and the second liquid L2 within the tube 20 from the outside. It is also preferable that the tube 20 is made of material having both water repellency and oleophilic property (such as PTFE). When the tube 20 is made of this type of material, the second liquid L2, which is an oil-base liquid, for example, easily forms a film on the surface of the tube 20. In this case, the first liquid L1, which is a water-base liquid, for example, does not easily adhere to the tube 20. Therefore, when a plurality of types of the first liquids L1 are used, for example, mixture between the respective types of the first liquids L1 can be prevented, which mixture may be caused when the first liquids L1 adhere to the inner wall of the tube 20.

It is preferable that at least the inner wall of the tube 20 has hydrophobic property. When at least the inner wall of the tube 20 has hydrophobic property, a liquid to be dispensed, which is a water-base liquid, for example, does not easily adhere to the tube 20. Moreover, the hydrophobic property of at least the inner wall of the tube 20 allows smoother shift of the water-base liquid within the tube 20 in the respective steps in this embodiment, thereby reducing the water-base liquid remaining within the tube 20 in the respective discharge steps. Accordingly, dispensation of liquid can be carried out with higher accuracy.

The inner wall of the tube 20 made of PTFE or polypropylene discussed above possesses hydrophobic property, for example. However, even when the tube 20 is made of low hydrophobic material, the inner wall of the tube 20 can obtain sufficient hydrophobic property through plasma treatment, hydrophobic substance coating or by other methods. Examples of this coating include hydrophobic silica whose surface has been treated by alkylsilane.

1.1.4. First Vessel

The first vessel 10 stores the first liquid L1 as a dispensation target of the dispensing method in this embodiment. According to the dispensing method in this embodiment, the first vessel 10 stores the second liquid L2 as well. The shape and the capacity of the first vessel 10 may be arbitrarily determined as long as the following conditions are met when the first liquid L1 and the second liquid L2 are stored in the first vessel 10, which conditions are: (1) the interface I12 is formed between the first liquid L1 and the second liquid L2 within the first vessel 10; (2) the first liquid L1 is positioned without contact with the atmosphere; and (3) the one end of the tube 20 inserted into the first vessel 10 reaches a position appropriate for the dispensing method described later. When the cross-sectional shapes of the opening of the first vessel 10 and the one end of the tube 20 are both circular, for example, a vessel whose opening diameter is larger than the diameter of the external shape of the one end of the tube 20 is appropriate for the first vessel 10. For example, the first vessel 10 is constituted by a test tube, a vial, or other vessels generally used in the biochemical field.

The first vessel 10 may be made of inorganic material (such as heat-resisting glass (Pyrex (registered trademark))), organic material (such as polycarbonate, polypropylene, and other resin), for example, or a composite of these materials. It is preferable that the first vessel 10 is made of material which transmits visible light such as glass, polycarbonate and polypropylene to allow visual observation of the interface I12 formed between the first liquid L1 and the second liquid L2 within the first vessel 10 from the outside.

1.1.5. Second Vessel

The second vessel 30 is a vessel into which the first liquid L1 dispensed by the dispensing method in this embodiment is introduced. According to the dispensing method in this embodiment, the second liquid L2 is also introduced into the second vessel 30. The shape of the second vessel 30 may be arbitrarily determined as long as the following conditions are met when the first liquid L1 and the second liquid L2 are introduced into the second vessel 30, which conditions are: (1) the interface I12 is formed between the first liquid L1 and the second liquid L2 within the second vessel 30; and (2) the first liquid L1 is positioned without contact with the atmosphere. According to the dispensing method in this embodiment, the plural second vessels 30 may be prepared. The second vessel 30 may be constituted by a test tube, a vial, or a vessel called "well" in the biochemical field, for example. When the second vessel 30 is a well, a plurality of (for example, 8×12=96 pieces of) wells corresponding to the second vessels 30 may be formed on a plate.

The second vessel 30 may be made of inorganic material (such as heat-resisting glass (Pyrex (registered trademark))), organic material (such as polycarbonate, polypropylene, and other resin), for example, or a composite of these materials.

When the second vessel 30 is used for purposes including observation of the interior of the second vessel 30 from the outside (such as real time PCR), the materials of the second vessel 30 may be transparent if necessary. The degree of "transparency" required herein is only a level sufficient for the purpose of use of the second vessel 30. For example, in case of visual observation, the second vessel 30 only needs to have a degree of transparency sufficient for allowing visual recognition of the interior. For the purpose of fluorometry in real time PCR or the like, the requirement is only a level sufficient for allowing optical measurement of fluorescence of the reaction liquid from the outside of the second vessel 30. Black substances such as carbon black, graphite, black titanium oxides, aniline black, oxides of Ru, Mn, Ni, Cr, Fe, Co, or Cu, and carbides of Si, Ti, Ta, Zr, or Cr, for example, may be added to the material of the second vessel 30 for fluorometry through the opening of the second vessel 30. The second vessel 30 mixed with these black substances can further reduce auto-fluorescence of resin or the like and thus increase the accuracy of PCR. When the second vessel 30 is used as a reaction vessel for PCR, it is preferable that the second vessel 30 is made of material absorbing less nucleic acids and proteins and not inhibiting reaction of enzymes such as polymerase.

1.2. Dispensing Method

The dispensing method according to this embodiment includes the first suction step, the second suction step, the third suction step, the first discharge step, the second discharge step, and the third discharge step.

1.2.1. First Suction Step

The first suction step (step S11) is a step for sucking the second liquid L2 into the tube 20 through the one end of the tube 20. The second liquid L2 to be sucked in the first suction step may be either the second liquid L2 stored in the first vessel 10 or the second liquid L2 stored in another vessel. The volume of the second liquid L2 sucked in the first suction step is not specifically limited. It is preferable, however, that the volume of the second liquid L2 is sufficient for eliminating the effect of the gas contained in the tube 20 on the first liquid L1 sucked in the second suction step.

After the first suction step, the second liquid L2 covers the area of the inner wall of the tube 20 brought into contact with the second liquid L2 during the first suction step. As a result, the first liquid L1 sucked in the second suction step is difficult to adhere to the inner wall of the tube 20, and therefore easily shifts within the tube 20. Moreover, the first suction step reduces the contact between the first liquid L1 sucked in the second suction step and the gas contained in the tube 20. FIG. 2A schematically illustrates a condition in which the second liquid L2 stored within the first vessel 10 is sucked through the one end of the tube 20 in the first suction step. After the first suction step, a liquid column of the second liquid L2 is formed at the one end of the tube 20.

1.2.2. Second Suction Step

The second suction step (step S12) is performed after the first step (step S11).

When the second liquid L2 is sucked from a vessel different from the first vessel 10 in the first suction step, for example, other steps such as the step for moving the tube 20 toward the first vessel 10 and inserting the one end of the tube 20 into the first vessel 10 may be carried out between the second suction step and the first suction step.

In the second suction step, the first liquid L1 positioned within the first vessel 10 and below the interface I12 between the first liquid L1 and the second liquid L2 is sucked into the tube 20 through the one end of the tube 20 located below the interface I12. The one end of the tube 20 positioned below the interface I12 in the second suction step corresponds to the one end of the tube 20 through which the second liquid L2 is sucked in the first suction step.

When the second liquid L2 contained in the first vessel 10 is sucked in the first suction step, the one end of the tube 20 is lowered to a position below the interface I12 before execution of the second suction step. The volume of the first liquid L1 sucked in the second suction step is not specifically limited. FIG. 2B schematically illustrates a condition in which the first liquid L1 stored in the first vessel 10 is sucked through the one end of the tube 20 in the second suction step. After the second suction step, a liquid column of the first liquid L1 is formed below the liquid column of the second liquid L2 at one end of the tube 20.

1.2.3. Third Suction Step

The third suction step (step S13) is continuously performed after the second suction step (step S12). The third suction step sucks the second liquid L2 into the tube 20 through the one end of the tube 20 positioned above the interface I12 within the first vessel 10. The one end of the tube 20 positioned above the interface I12 in the third suction step corresponds to the one end of the tube 20 through which the first liquid L1 is sucked in the second suction step.

In this specification, the expression "A step is continuously performed after B step" refers to an operation in which A step is carried out for the vessel under the condition as it is after execution of B step. In addition, the expression "A step is performed after B step" refers to both an operation in which A step is continuously carried out after B step and an operation in which other step or steps are carried out between A step and B step.

The volume of the second liquid L2 sucked in the third suction step is not specifically limited. When the second liquid L2 is not stored within the second vessel 30 beforehand in the first discharge step, it is preferable that the volume of the second liquid L2 sucked in the third suction step is larger than the minimum volume of the second liquid L2 in which the opening at the one end of the tube 20 can soak after discharge of the second liquid L2 in the first discharge step.

FIG. 2C schematically illustrates a condition in which the second liquid L2 stored in the first vessel 10 is sucked through the one end of the tube 20 in the third suction step. After the third suction step, the liquid column of the first liquid L1 comes into such a condition as to be sandwiched between the two liquid columns of the second liquid L2.

FIG. 2D illustrates a condition of the tube 20 after the third suction step. As can be seen from FIG. 2D, the tube 20 after the third suction step contains the liquid columns of the second liquid L2, the first liquid L1, and the second liquid L2 in this order from the one end of the tube 20. Thus, the tube 20 can be moved substantially without contact between the first liquid L1 and the air.

1.2.4. First Discharge Step

The first discharge step (step S21) is performed after the third suction step (step S13).

Between the third suction step and the first discharge step, at least the step for moving the tube 20 from the first vessel 10 toward the second vessel 30 is carried out. Other step or steps may be performed between the third suction step and the first discharge step.

The first discharge step releases the second liquid L2 sucked into the tube 20 in the third suction step (step S13) to discharge this second liquid L2 into the second vessel 30 through the one end of the tube 20. The one end of the tube 20 through which the second liquid L2 is discharged in the first discharge step corresponds to the one end of the tube 20 through which the second liquid L2 is sucked in the third suction step.

After the first discharge step, the opening at the one end of the tube 20 soaks in the second liquid L2 discharged into the second vessel 30. Under the condition in which the opening at the one end of the tube 20 soaks in the second liquid L2 by the first discharge step, contact between the first liquid L1 discharged in the second discharge step and the air is avoided. Moreover, under the condition in which the opening at the one end of the tube 20 soaks in the second liquid L2, the first liquid L1 discharged in the second discharge step can be easily discharged from the tube 20.

The second liquid L2 may be stored beforehand in the second vessel 30 into which the second liquid L2 is discharged in the first discharge step. In this case, the opening at the one end of the tube 20 can easily soak in the second liquid L2 before and after the period of the first discharge step, wherefore contact between the first liquid L1 discharged in the second discharge step and the air can be further prevented. Moreover, when the second liquid L2 is stored in the second vessel 30 in advance, the first liquid L1 can be more easily discharged in the second discharge step.

FIG. 3A illustrates a condition in which the tube 20 is positioned within the second vessel 30 after the third suction step. FIG. 3B illustrates a condition after completion of the first discharge step, showing the liquid columns of the first liquid L1 and the second liquid L2 remaining within the tube 20.

1.2.5. Second Discharge Step

The second discharge step (step S22) is continuously performed after the first discharge step (step S21). The second discharge step releases the first liquid L1 sucked into the tube 20 in the second suction step (step S12) to discharge this first liquid L1 into the second vessel 30 through the one end of the tube 20. The one end of the tube 20 through which the first liquid L1 is discharged in the second discharge step corresponds to the one end of the tube 20 through which the first liquid L1 is sucked in the second suction step.

The second discharge step is carried out under the condition in which the opening at the one end of the tube 20 soaks in the second liquid L2. Under this condition, contact between the first liquid L1 discharged in the second discharge step and the air is avoided. Moreover, under the condition in which the opening at the one end of the tube 20 soaks in the second liquid L2, the first liquid L1 can be easily discharged from the tube 20 in the second discharge step.

FIG. 3C illustrates a condition after completion of the second discharge step. In this condition, the first liquid L1 comes out of the tube 20 while contacting the one end of the tube 20, but the liquid column of the second liquid L2 still remains within the tube 20. The second discharge step is performed under the condition in which the opening at the one end of the tube 20 soaks in the second liquid L2 contained within the second vessel 30. Thus, contact between the first liquid L1 and the air is avoided.

1.2.6. Third Discharge Step

The third discharge step (step S23) is continuously performed after the second discharge step (step S22). The third discharge step releases at least a part of the second liquid L2 sucked into the tube 20 in the first suction step (step S11) to discharge this second liquid L2 into the second vessel 30 through the one end of the tube 20. The one end of the tube 20 through which the second liquid L2 is discharged in the third discharge step corresponds to the one end of the tube 20 through which the second liquid L2 is sucked in the first suction step.

The third discharge step is performed under the condition in which the opening at the one end of the tube 20 soaks in the second liquid L2. In this case, the second liquid L2 discharged in the third discharge step joins the second liquid L2 existing within the second vessel 30, whereby the first liquid L1 discharged in the second discharge step separates from the tube 20.

The second liquid L2 discharged in the third discharge step may be either a part or the whole of the second liquid L2 sucked into the tube 20 in the first suction step.

FIG. 3D illustrates a condition in which a part of the second liquid L2 is discharged after the third discharge step. After completion of the third discharge step, the liquid column of the second liquid L2 remains within the tube 20, while the first liquid L1 is separated from the tube 20. In the third discharge step performed under the condition in which the opening at the one end of the tube 20 soaks in the second liquid L2 contained in the second vessel 30, the first liquid L1 is difficult to contact the air. Moreover, in the third discharge step performed under the condition in which the opening at the one end of the tube 20 soaks in the second liquid L2 contained in the second vessel 30, the liquid column of the second liquid L2 within the tube 20 can be combined with the second liquid L2 existing within the second vessel 30 as illustrated in the figure. In this condition, the first liquid L1 can be easily separated from the opening at the one end of the tube 20. FIG. 3D shows an example of the first liquid L1 forming a liquid drop after separation.

1.2.7. Modified Example

According to the first embodiment, the dispensing method which dispenses the first liquid L1 contained in the one first vessel 10 into the one second vessel 30 has been discussed. However, the dispensing method in the first embodiment may be modified into such a method which dispenses the first liquid L1 contained in the one first vessel 10 into a plurality of the second vessels 30. A modified example which dispenses the first liquid L1 contained in the one first vessel 10 into the two second vessels 30 is now explained.

The dispensing method according to this modified example includes the first suction step, the second suction step, the third suction step, the first discharge step, the second discharge step, and the third discharge step. The respective steps in this example are similar to the corresponding steps in the first embodiment, and the same explanation is not repeated. According to the dispensing method in this modified example, the steps included in a part A in the flowchart shown in FIG. 1 (second suction step and third suction step) are performed a plurality of times. Then, after the third suction step performed last in the part A, the steps included in a part B (first discharge step, second discharge step, and third discharge step) are performed a plurality of times.

After completion of the third suction step in the first embodiment, the second suction step and the third suction step are again executed. As a result, liquid columns of the second liquid L2, the first liquid L1, the second liquid L2, the first liquid L1, and the second liquid L2 are formed within the tube 20 in this order from the one end of the tube 20 at the end of the third suction step performed second. The tube 20 can be moved without changing this condition.

Then, the first discharge step, the second discharge step, and the third discharge step are conducted for the second vessel 30 to be handled first so as to dispense the first liquid L1 sucked in the second suction step performed second into this second vessel 30. In this case, a condition similar to the condition after completion of the third suction step in the first embodiment can be produced when a part of the second liquid L2 is left within the tube 20 in the third suction step. Under this condition, the tube 20 is moved toward the second vessel 30 to be handled second, and the first discharge step, the second discharge step, and the third discharge step are conducted for the second vessel 30 to be handled second so as to dispense the first liquid L1 sucked in the second suction step performed first into this second vessel 30.

When this method is applied to dispensation using a dispensing device or the like, the number of times of the shift of the tube 20 between the first vessel 10 and the second vessel 30 can be reduced. In this case, the step for moving the tube 20 can be eliminated, wherefore the time required for dispensing processes can be shortened. When suction and discharge of liquid is carried out with the aid of a pump, a long time is required for switching between suction and discharge in some cases. According to this modified example which can reduce the number of times of this switching, the time required for dispensing processes can be shortened even when a pump is used.

1.3. Advantages

According to the dispensing method in this embodiment, the first liquid L1 contained in the first vessel 10 and during the respective suction steps and discharge steps is sealed by the second liquid L2, and therefore is difficult to contact a gaseous phase (such as air). In other words, during shift of the first liquid L1 from the first vessel 10 to the second vessel 30 for dispensation according to the dispensing method in this embodiment, the first liquid L1 is handled in the condition of contact with the second liquid L2 and therefore is difficult to contact the air and the like. In this case, evaporation of the constituent components of the first liquid L1 into a gaseous phase, and entrance of other substances such as water through a gaseous phase into the first liquid L1 can be prevented. Accordingly, variations in the concentrations of the solvent and solutes of the first liquid L1 decrease, which contributes to accurate dispensation.

Moreover, according to the dispensing method in this embodiment, the first liquid L1 is discharged into the second liquid L2 in the second discharge step (step S22). In this case, the first liquid L1 does not easily remain within the tube 20 or in the vicinity of the one end of the tube 20 in the second discharge step. Accordingly, the first liquid L1 contained in the first vessel 10 can be accurately dispensed into the second vessel 30.

2. Second Embodiment

Figure 4:
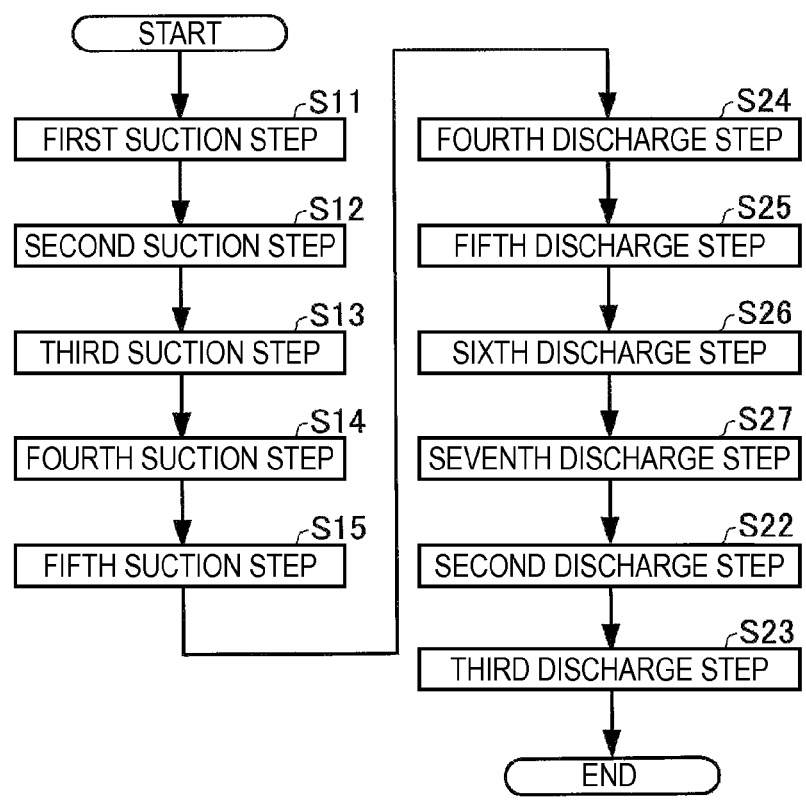
FIG. 4 is a flowchart showing the flow of a dispensing method according to a second embodiment.
Figures 5A, 5B, 5C, 5D:
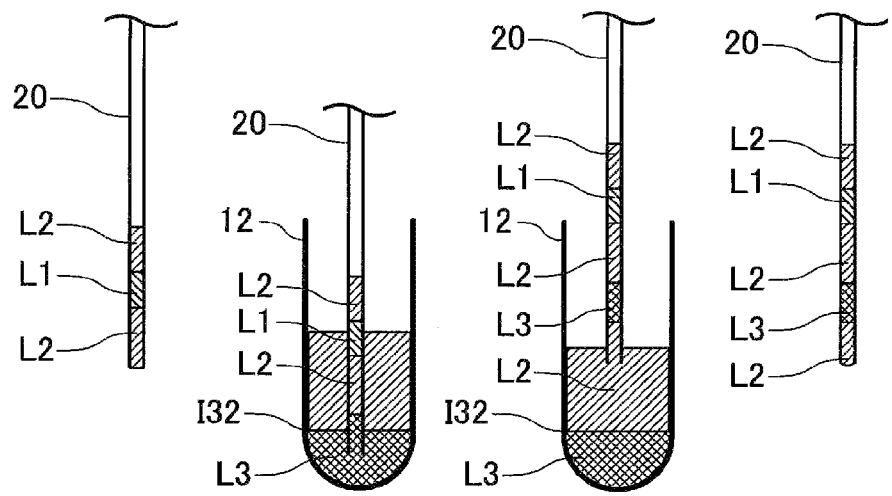
FIG. 5A schematically illustrates a preparatory condition before a fourth suction step according to the second embodiment.
FIG. 5B schematically illustrates the fourth suction step according to the second embodiment.
FIG. 5C schematically illustrates a fifth suction step according to the second embodiment.
FIG. 5D schematically illustrates a condition of a tube after the fifth suction step according to the second embodiment.

A dispensing method according to a second embodiment of the invention is hereinafter described. FIG. 4 is a flowchart showing the flow of the dispensing method in this embodiment. Each of FIGS. 5A through 5D schematically illustrates a part of the steps performed in the dispensing method in this embodiment. FIG. 5A schematically illustrates a preparatory condition of a fourth suction step in this embodiment. FIG. 5B schematically illustrates the fourth suction step in this embodiment. FIG. 5C schematically illustrates a fifth suction step in this embodiment. FIG. 5D schematically illustrates a condition of the tube after the fifth suction step.

2.1. Structure

The dispensing method according to this embodiment is a method for dispensing the first liquid L1 contained in the first vessel 10 which stores the first liquid L1 and the second liquid L2, and a third liquid L3 contained in a third vessel 12 which stores the second liquid L2 and the third liquid L3 to introduce these first liquid L1 and the third liquid L3 into the second vessel 30 via the tube 20.

The first liquid L1, the second liquid L2, the first vessel 10, and the tube 20 are similar to the corresponding liquids and components used in the first embodiment. Thus, these liquids and components in this embodiment have been given similar reference numbers, and the same explanation is not repeated.

2.1.1. Third Liquid

The third liquid L3 is a liquid not miscible with the second liquid L2. In addition, the third liquid L3 is a liquid having higher specific gravity than that of the second liquid L2. When the third liquid L3 having these characteristics is used, a (phase-separation) interface I32 is produced between the third liquid L3 and the second liquid L2 coexisting within the third vessel 12 as illustrated in FIGS. 5B and 5C. In this case, the third liquid L3 is positioned below the interface I32 (bottom side of the third vessel 12), while the second liquid L2 is positioned above the interface I32 (opening side of the third vessel 12). Moreover, the third liquid L3 has surface tension, and becomes a liquid drop within the second liquid L2 when the volume of the third liquid L3 is sufficiently small. The third liquid L3 may be either a liquid of water-base type or of oil-base type. When the third liquid L3 is a water-base type liquid, for example, the second liquid L2 may be of oil-base type. Conversely, the third liquid L3 and the second liquid L2 may be an oil-base type third liquid and a water-base type liquid, respectively.

The third liquid L3 may be a solution used for preparing a reaction liquid for PCR. When the third liquid L3 is a solution used for preparing a reaction liquid for PCR, the third liquid L3 may contain nucleic acids (target nucleic acids), or at least one type of reagents necessary for causing reaction. In this case (or in other cases), a part of the remaining reagents may be contained in the second vessel 30 beforehand. Moreover, the third liquid L3 may be a solution containing substances easily oxidized by oxygen in the atmosphere, or substances easily reacting to molecules such as those of water contained in the atmosphere.

2.1.2. Third Vessel

The third vessel 12 is substantially similar to the first vessel 10 used in the first embodiment. The third vessel 12 is a vessel into which the third liquid L3 is dispensed by the dispensing method in this embodiment.

According to the dispensing method in this embodiment, the third vessel 12 contains the second liquid L2 as well. The shape of the third vessel 12 is arbitrarily determined as long as the following conditions are met when the third liquid L3 and the second liquid L2 are introduced into the third vessel 12, which conditions are: (1) the interface I32 is formed between the third liquid L3 and the second liquid L2 within the third vessel 12; and (2) the third liquid L3 is contained without contact with the atmosphere. The third vessel 12 may be a test tube, a vial, or a vessel generally used in the biochemical field, for example. The material of the third vessel 12 is similar to that of the first vessel 10.

2.2. Dispensing Method

The dispensing method in this embodiment includes the first suction step, the second suction step, the third suction step, the fourth suction step, the fifth suction step, a fourth discharge step, a fifth discharge step, a sixth discharge step, a seventh discharge step, the second discharge step, and the third discharge step.

The first suction step, the second suction step, the third suction step, the second discharge step, and the third discharge step are similar to the corresponding steps in the first embodiment except that the second discharge step is continuously performed after the seventh discharge step. Thus, these steps in this embodiment have been given similar reference numbers, and the same explanation is not repeated. According to the dispensing method in this embodiment, the first suction step through the third suction step (step S13) are carried out in the same manner as in the first embodiment, and then the following steps are executed.

FIG. 5A illustrates a condition of the tube 20 after the third suction step (step S13) in the dispensing method in this embodiment. As can be seen from FIG. 5A, liquid columns of the second liquid L2, the first liquid L1, and the second liquid L2 are formed within the tube 20 in this order from the one end of the tube 20 after the third suction step. The tube 20 can be moved without changing this condition.

2.2.1. Fourth Suction Step

The fourth suction step (step S14) is performed after the third suction step (step S13).

Between the fourth suction step and the third suction step, other steps such as the step for moving the tube 20 toward the third vessel 12 and inserting the one end of the tube 20 into the third vessel 12 may be carried out.

In the fourth suction step, the third liquid L3 is sucked through the one end of the tube 20 positioned below the interface I32 between the third liquid L3 and the second liquid L2 within the third vessel 12.

The one end of the tube 20 positioned below the interface I32 in the fourth suction step corresponds to the one end of the tube 20 through which the second liquid L2 is sucked in the third suction step. The volume of the third liquid L3 sucked in the fourth suction step is not specifically limited.

FIG. 5B schematically illustrates a condition in which the third liquid L3 contained in the third vessel 12 is sucked through the one end of the tube 20 in the fourth suction step. After the fourth suction step, a liquid column of the third liquid L3 is formed at the one end of the tube 20 on the side of the liquid column of the second liquid L2 opposite to the side where the liquid column of the first liquid L1 is formed.

2.2.2. Fifth Suction Step

The fifth suction step (step S15) is continuously performed after the fourth suction step (step S14). In the fifth suction step, the second liquid L2 is sucked through the one end of the tube 20 positioned above the interface I32 within the third vessel 12. The one end of the tube 20 positioned above the interface I32 in the fifth suction step corresponds to the one end of the tube 20 through which the third liquid L3 is sucked in the fourth suction step.

The volume of the second liquid L2 sucked in the fifth suction step is not specifically limited. When the second liquid L2 is not contained in the second vessel 30 beforehand in the fourth discharge step, it is preferable that the volume of the second liquid L2 sucked in the fifth suction step is larger than the minimum volume of the second liquid L2 in which the opening at the one end of the tube 20 can soak after discharge of the second liquid L2 in the fourth discharge step.

FIG. 5C schematically illustrates a condition in which the second liquid L2 contained in the third vessel 12 is sucked through the one end of the tube 20 in the fifth suction step. After the fifth suction step, a liquid column of the second liquid L2 is formed at the one end of the tube 20 below the liquid column of the third liquid L3. FIG. 5D illustrates a condition of the tube 20 after the fifth suction step. As can be seen from FIG. 5D, liquid columns of the second liquid L2, the third liquid L3, the second liquid L2, the first liquid L1, and the second liquid L2 are formed within the tube 20 in this order from the one end of the tube 20 after the fifth suction step. The tube 20 can be moved without changing this condition.

2.2.3. Fourth Discharge Step

The fourth discharge step (step S24) is performed after the fifth suction step (step S15).

Between the fifth suction step and the fourth discharge step, at least the step for moving the tube 20 from the third vessel 12 toward the second vessel 30 is carried out. Other step or steps may be executed between the fifth suction step and the fourth discharge step.

In the fourth discharge step, the second liquid L2 sucked into the vessel 20 in the fifth suction step (step S15) is discharged into the second vessel 30 through the one end of the tube 20. The one end of the tube 20 through which the second liquid L2 is discharged in the fourth discharge step corresponds to the one end of the tube 20 through which the second liquid L2 is sucked in the fifth suction step.

After the fourth discharge step, the opening at the one end of the tube 20 soaks in the second liquid L2 discharged into the second vessel 30. Under the condition in which the opening at the one end of the tube 20 soaks after the fourth discharge step, contact between the third liquid L3 discharged in the fifth discharge step and the air is avoided. Moreover, under the condition in which the opening at the one end of the tube 20 soaks in the second liquid L2, the third liquid L3 discharged in the fifth discharge step is easily discharged from the tube 20. The second liquid L2 may be stored beforehand in the second vessel 30 into which the second liquid L2 is discharged in the fourth discharge step. In this case, the opening at the one end of the tube 20 can easily soak in the second liquid L2 before and after the period of the fourth discharge step, wherefore contact between the third liquid L3 discharged in the fifth discharge step and the air can be further prevented. Moreover, when the second liquid L2 is stored in the second vessel 30 in advance, the third liquid L3 can be more easily discharged from the tube 20 in the fifth discharge step.

2.2.4. Fifth Discharge Step

The fifth discharge step (step S25) is continuously performed after the fourth discharge step (step S24). In the fifth discharge step, the third liquid L3 sucked into the tube 20 in the fourth suction step (step S14) is discharged into the second vessel 30 through the one end of the tube 20. The one end of the tube 20 through which the third liquid L3 is discharged in the fifth discharge step corresponds to the one end of the tube 20 through which the third liquid L3 is sucked in the fourth suction step.

The fifth discharge step is performed in the condition in which the opening at the one end of the tube 20 soaks in the second liquid L2. Under this condition, contact between the third liquid L3 discharged in the fifth discharge step and the air is avoided. Moreover, similarly to the second discharge step, under the condition in which the opening at the one end of the tube 20 soaks in the second liquid L2, the third liquid L3 can be easily discharged from the tube 20 in the fifth discharge step.

2.2.5. Sixth Discharge Step

The sixth discharge step (step S26) is continuously performed after the fifth discharge step (step S25). In the sixth discharge step, a part of the second liquid L2 sucked into the tube 20 in the third suction step (step S13) is discharged into the second vessel 30 through the one end of the tube 20. The one end of the tube 20 through which the second liquid L2 is discharged in the sixth discharge step corresponds to the one end of the tube 20 through which the second liquid L2 is sucked in the third suction step.

The sixth discharge step is executed in the condition in which the opening at the one end of the tube 20 soaks in the second liquid L2. Under this condition, the second liquid L2 discharged in the sixth discharge step joins the second liquid L2 contained in the second vessel 30, whereby the third liquid L3 discharged in the fifth discharge step can separate from the tube 20. The second liquid L2 discharged in the sixth discharge step corresponds to a part of the second liquid L2 sucked into the tube 20 in the third suction step. Thus, after completion of the sixth discharge step, liquid columns of the second liquid L2, the first liquid L1, and the second liquid L2 are formed within the tube 20 in this order from the one end of the tube 20. The tube 20 can be moved without changing this condition.

2.2.6. Seventh Discharge Step

The seventh discharge step (step S27) is performed after the sixth discharge step (step S26).

Between the sixth discharge step and the seventh discharge step, the step for moving the tube 20 toward the second vessel 30 different from the second vessel 30 handled in the sixth discharge step may be carried out. The seventh discharge step may be executed either for the second vessel 30 identical to the second vessel 30 handled in the sixth discharge step, or the second vessel 30 different from the second vessel 30 handled in the sixth discharge step.

When the seventh discharge step is performed for the second vessel 30 identical to the second vessel 30 for which the sixth discharge step has been conducted, the first liquid L1 and the third liquid L3 can be mixed with each other within this second vessel 30. On the other hand, when the seventh discharge step is performed for the second vessel 30 different from the second vessel 30 for which the sixth discharge step has been conducted, the first liquid L1 and the third liquid L3 can be dispensed into the one and the other second vessels 30, respectively. In the seventh discharge step, the part of the second liquid L2 sucked into the tube 20 in the third suction step (step S13) and remaining within the tube 20 after the sixth discharge step is discharged into the second vessel 30 through the one end of the tube 20. The one end of the tube 20 through which the second liquid L2 is discharged in the seventh discharge step corresponds to the one end of the tube 20 through which the second liquid L2 is sucked in the third suction step.

After the seventh discharge step, the opening at the one end of the tube 20 soaks in the second liquid L2 discharged into the second vessel 30. Under the condition in which the opening at the one end of the tube 20 soaks in the second liquid L2 after the seventh discharge step, contact between the first liquid L1 discharged in the second discharge step and the air is avoided. Moreover, under the condition in which the opening at the one end of the tube 20 soaks in the second liquid L2, the first liquid L1 can be easily discharged from the tube 20 in the second discharge step.

The second liquid L2 may be stored beforehand in the second vessel 30 into which the second liquid L2 is discharged in the seventh discharge step. In this case, the opening at the one end of the tube 20 can easily soak in the second liquid L2 before and after the period of the seventh discharge step, wherefore contact between the first liquid L1 discharged in the second discharge step and the air can be further prevented. Moreover, when the second liquid L2 is stored in the second vessel 30 in advance, the first liquid L1 can be more easily discharged from the tube 20 in the second discharge step.

According to the dispensing method in this embodiment, the second discharge step and the third discharge step are performed after the seventh discharge step similarly to the first embodiment.

2.3. Advantages

According to the dispensing method in this embodiment, the first liquid L1 and the third liquid L3 contained in the first vessel 10 and the third vessel 12, and during the respective suction steps and discharge steps are sealed by the second liquid L2. Therefore, the first liquid L1 and the third liquid L3 are difficult to contact a gaseous phase (such as air). In other words, during dispensation by the dispensing method in this embodiment, the first liquid L1 and the third liquid L3 are handled in the condition of contact with the second liquid L2 and therefore is difficult to contact the air and the like. In this case, evaporation of the constituent components of the first liquid L1 and the third liquid L3 into a gaseous phase, and entrance of other substances such as water through a gaseous phase into the first liquid L1 and the third liquid L3 can be prevented. Accordingly, variations in the concentrations of the first liquid L1 and the third liquid L3 decrease, which contributes to accurate dispensation.

Moreover, according to the dispensing method in this embodiment, the third liquid L3 is discharged into the second liquid L2 in the fifth discharge step (step S25), and the first liquid L1 is discharged into the second liquid L2 in the second discharge step (step S22). In this case, the third liquid L3 and the first liquid L1 are difficult to remain within the tube 20 or in the vicinity of the one end of the tube 20 in the fifth discharge step and the second discharge step. Accordingly, the first liquid L1 and the third liquid L3 can be accurately dispensed into the second vessel 30.

Furthermore, according to the dispensing method in this embodiment, the third liquid L3 and the first liquid L1 are surrounded by the second liquid L2 while handled. In this case, the third liquid L3 and the first liquid L1 do not easily mix with each other, wherefore a plurality of types of liquids can be dispensed via the one tube 20. Accordingly, similarly to the modified example of the first embodiment, a plurality of types of liquids can be dispensed into a plurality of the second vessels 30 with one-to-one correspondence, or can be dispensed into the one second vessel 30 according to the method of this embodiment.

3. Third Embodiment

Figure 6:
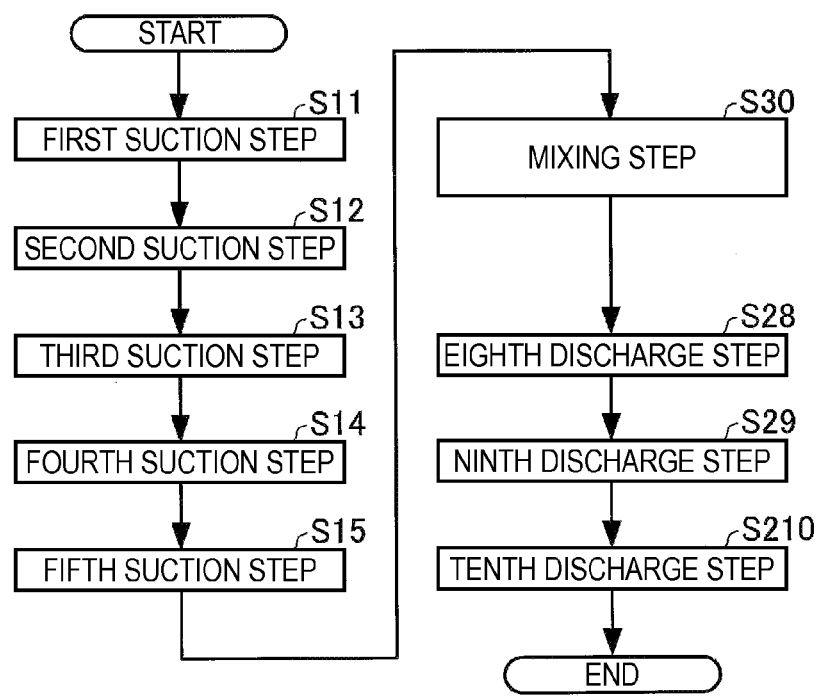
FIG. 6 is a flowchart showing the flow of a dispensing method according to a third embodiment.
Figures 7A, 7B, 7C, 7D, 7E:
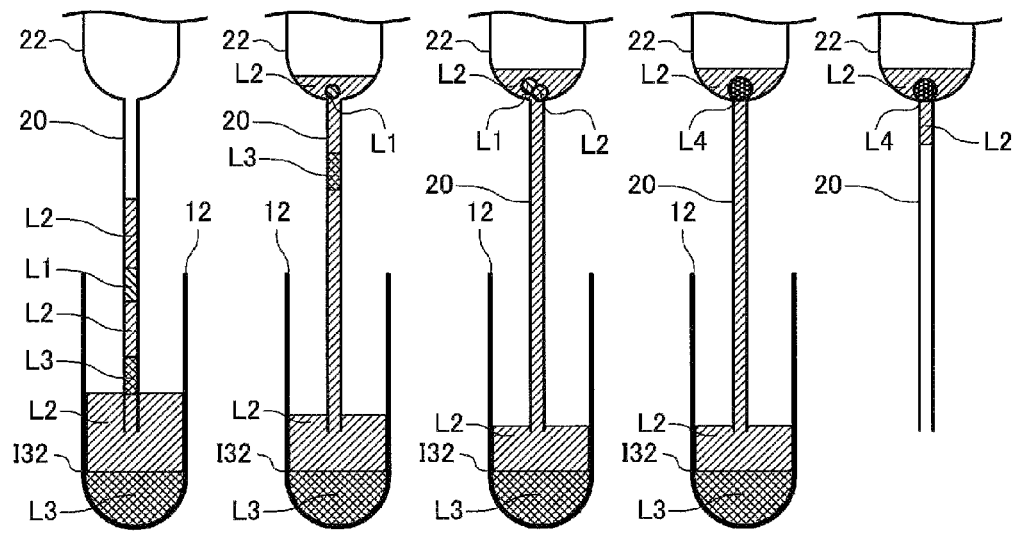
FIG. 7A schematically illustrates a fifth suction step according to the third embodiment.
FIGS. 7B and 7C schematically illustrate a mixing step according to the third embodiment.
FIGS. 7D and 7E schematically illustrates a condition after the mixing step according to the third embodiment.
Figures 8A, 8B:
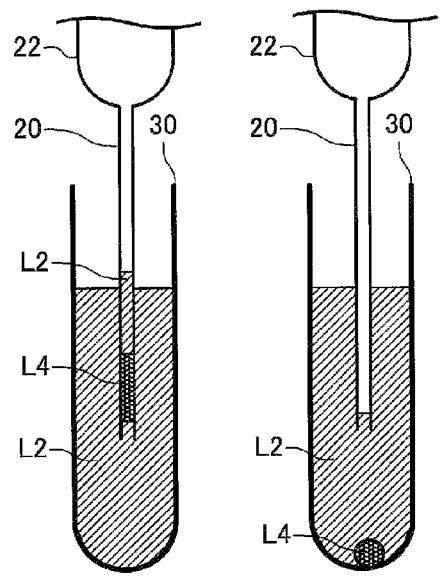
FIG. 8A schematically illustrates an eighth discharge step according to the third embodiment.
FIG. 8B schematically illustrates a tenth discharge step according to the third embodiment.

A dispensing method according to the third embodiment of the invention is hereinafter described. FIG. 6 is a flowchart showing the flow of this dispensing method. Each of FIGS. 7A through 7E and FIGS. 8A and 8B schematically illustrates a part of the steps performed in the dispensing method in this embodiment. FIG. 7A schematically illustrates the fifth suction step in this embodiment. FIGS. 7B and 7C schematically illustrate a mixing step in this embodiment. FIGS. 7D and 7E schematically illustrate a condition after the mixing step in this embodiment. FIG. 8A schematically illustrates an eighth discharge step in this embodiment. FIG. 8B schematically illustrates a tenth discharge step in this embodiment.

3.1. Structure

The dispersing method in this embodiment is a method for dispersing the first liquid L1 contained in the first vessel 10 which stores the first liquid L1 and the second liquid L2, and the third liquid L3 contained in the third vessel 12 which stores the second liquid L2 and the third liquid L3 to introduce these first liquid L1 and the third liquid L3 into the second vessel 30 through the tube 20 the one end of which is opened and the other end of which is connected with a reservoir 22.

The first liquid L1, the second liquid L2, the third liquid L3, the first vessel 10, the third vessel 12, and the tube 20 are similar to the corresponding liquids and components used in the first and second embodiments. Thus, these liquids and components in this embodiment have been given similar reference numbers, and the same explanation is not repeated. According to this embodiment, the reservoir 22 is connected with the other end of the tube 20.

3.1.1. Reservoir

The reservoir 22 is connected with the other end of the tube 20. The reservoir 22 is a chamber which has a larger inside diameter than that of the tube 20. The reservoir 22 may be either a component formed integrally with the tube 20, or a component detachably attached to the tube 20. Even when the reservoir 22 is connected with the tube 20, liquid can be sucked from the other end of the tube 20 via the reservoir 22 by the use of a pump or the like connected to a position of the reservoir 22 different from the attachment position between the tube 20 and the reservoir 22.

The shape of the reservoir 22 may be arbitrarily determined as long as the liquids within the tube 20 sucked through the other end of the tube 20 into the reservoir 22 do not form plugs within the reservoir 22.

At the time of supply of the liquids from the reservoir 22 to the tube 20, the liquids within the reservoir 22 are sent to the tube 20 in the order of specific gravity independently of the order of suction of the liquids from the tube 20 into the reservoir 22 due to the lack of plugs of the liquids within the reservoir 22. The method for suction and pressurization within the reservoir 22 is similar to the method shown in the explanation of the tube 20. The material of the reservoir 22 is similar to the material of the tube 20.

It is preferable that at least the inner wall of the reservoir 22 has hydrophobic property. When at least the inner wall of the reservoir 22 has hydrophobic property, the liquid to be dispensed, provided that this liquid is of water-base type, does not easily adhere to the reservoir 22.

3.2. Dispensing Method

The dispensing method in this embodiment includes the first suction step, the second suction step, the third suction step, the fourth suction step, the fifth suction step, the mixing step, the eighth discharge step, the ninth discharge step, and the tenth discharge step.

The first suction step, the second suction step, the third suction step, the fourth suction step, and the fifth suction step are similar to the corresponding steps performed in the first embodiment and the second embodiment. Thus, these steps in this embodiment have been given similar reference numbers, and the same explanation is not repeated. According to the dispensing method in this embodiment, the steps up to the fifth suction step (step S15) are carried out in the same manner as in the second embodiment, and then the following steps are executed.

FIG. 7A illustrates a condition of the tube 20 inserted into the third vessel 12 after the fifth suction step (step S15). As can be seen from FIG. 7A, liquid columns of the second liquid L2, the third liquid L3, the second liquid L2, the first liquid L1, and the second liquid L2 are formed within the tube 20 in this order from the one end of the tube 20 after the fifth suction step.

3.2.1. Mixing Step

The mixing step (step S30) is performed during the fifth suction step (step S15) or after the fifth suction step (step S15). FIGS. 7B through 7D show an example of the mixing step performed during the fifth suction step. FIG. 7E illustrates the mixing step performed after the tube is moved in the atmosphere subsequent to completion of the fifth suction step.

In the mixing step, the respective liquids within the tube 20 (the second liquid L2 sucked in the first suction step, the first liquid L1 sucked in the second suction step, the second liquid L2 sucked in the third suction step, the third liquid L3 sucked in the fourth suction step, and a part of the second liquid L2 sucked in the fifth suction step if necessary) are sucked into the reservoir 22 in such a manner that at least a part of the second liquid L2 sucked in the fifth suction step remains within the tube 20. Then, the first liquid L1 sucked into the tube 20 in the second suction step, and the third liquid L3 sucked into the tube 20 in the fourth suction step are mixed within the reservoir 22 to be formed into a fourth liquid L4. Simultaneously, the second liquid L2 sucked in the first suction step, the second liquid L2 sucked in the third suction step, and the second liquid L2 sucked in the fifth suction step if necessary are mixed with each other.

In this specification, the expression "A step is performed during B step" refers to the operation in which A step is performed within the period of the B step. Thus, the mixing step performed during the fifth suction step in this embodiment is a mixing step carried out while the second liquid L2 is being sucked into the tube 20 in the fifth suction step. On the other hand, the mixing step performed after the fifth suction step in this embodiment is a mixing step carried out while gas or other liquid is being sucked into the tube 20.

When the second liquid L2 sucked in the first suction step and the first liquid L1 sucked in the second suction step are introduced into the reservoir 22 as illustrated in FIG. 7B, the plug shape of the first liquid L1 changes into a liquid drop within the reservoir 22. With continuation of suction as illustrated in FIG. 7C, the second liquid L2 sucked in the third suction step and the third liquid L3 sucked in the fourth suction step are introduced into the reservoir 22. The two parts of the second liquid L2 introduced into the reservoir 22 join each other, whereby the liquid drops of the first liquid L1 and the third liquid L3 having higher specific gravity than that of the second liquid L2 contact each other within the reservoir 22. Then, as illustrated in FIG. 7D, a liquid drop of the fourth liquid L4 as a mixed liquid of the first liquid L1 and the third liquid L3 is produced within the reservoir 22. Even under this condition, the fourth liquid L4 having higher specific gravity than that of the second liquid L2 is surrounded by the second liquid L2 and thus is difficult to contact the air while contained in the reservoir 22. It is preferable that the mixture is executed under the condition in which the connection side of the reservoir 22 with the tube 20 is positioned on the lower side. In this condition, contact between the air and the first liquid L1, the third liquid L3, and the fourth liquid L4 can be further prevented even when the air is contained in the reservoir 22. The fourth liquid L4 is a liquid of mixture of the first liquid L1 and the third liquid L3. When the first liquid L1 is a water solution containing nucleic acids as an amplification target of PCR which uses the second liquid L2 as reagents necessary for causing reaction of PCR, the fourth liquid L4 corresponds to a reaction liquid for PCR.

After the mixing step, the liquid drop of the fourth liquid L4 and the second liquid L2 coexist within the reservoir 22, and the liquid column of the second liquid L2 sucked in the fifth suction step remains within the tube 20. The tube 20 can be moved without changing this condition.

3.2.2. Eighth Discharge Step

The eighth discharge step (step S28) is performed after the mixing step (step S30). In the eighth discharge step, the second liquid L2 sucked into the tube 20 in the fifth suction step (step S15) and still remaining within the tube 20 after the mixing step is discharged into the second vessel 30 through the one end of the tube 20. Other step or steps may be performed between the mixing step and the eighth discharge step. The one end of the tube 20 through which the second liquid L2 is discharged in the eighth discharge step corresponds to the one end of the tube 20 through which the second liquid L2 is sucked in the fifth suction step.

After the eighth discharge step, the opening at the one end of the tube 20 soaks in the second liquid L2 discharged into the second vessel 30. Under the condition in which the opening at the one end of the tube 20 soaks in the second liquid L2 after the eighth discharge step, contact between the fourth liquid L4 discharged in the ninth discharge step and the air is avoided. Moreover, under the condition in which the opening at the one end of the tube 20 soaks in the second liquid L2, the fourth liquid L4 discharged in the ninth discharge step is easily discharged from the tube 20.

The second liquid L2 may be stored beforehand in the second vessel 30 into which the second liquid L2 is discharged in the eighth discharge step. In this case, the opening at the one end of the tube 20 can easily soak in the second liquid L2 before and after the period of the eighth discharge step, wherefore contact between the fourth liquid L4 discharged in the ninth discharge step and the air can be further prevented. Moreover, when the second liquid L2 is stored in the second vessel 30 in advance, the fourth liquid L4 can be more easily discharged from the tube 20 in the ninth discharge step.

FIG. 8A illustrates a condition in which the tube 20 is inserted into the second vessel 30 in the eighth discharge step. FIG. 8A shows the case in which the second liquid L2 is contained in the second vessel 30 beforehand.

3.2.3. Ninth Discharge Step

The ninth discharge step (step S29) is continuously performed after the eighth discharge step (step S28). In the ninth discharge step, the fourth liquid L4 produced within the reservoir 22 by the mixing step (step S30) is discharged into the second vessel 30 through the one end of the tube 20. The one end of the tube 20 through which the fourth liquid L4 is discharged in the ninth discharge step corresponds to the end of the tube 20 to which the reservoir 22 is not connected.

The ninth discharge step is carried out under the condition in which the opening at the one end of the tube 20 soaks in the second liquid L2 contained in the second vessel 30. In this case, contact between the air and the fourth liquid L4 discharged in the ninth discharge step can be prevented. Moreover, under the condition in which the opening at the one end of the tube 20 soaks in the second liquid L2, the fourth liquid L4 can be discharged from the tube 20 in the ninth discharge step similarly to the second discharge step.

3.2.4. Tenth Discharge Step

The tenth discharge step (step S210) is continuously performed after the ninth discharge step (step S29). In the tenth discharge step, at least a part of the second liquid L2 mixed in the mixing step (step S30) is discharged into the second vessel 30 through the one end of the tube 20. The one end of the tube 20 through which the second liquid L2 is discharged in the tenth discharge step corresponds to the one end of the tube 20 through which the second liquid L2 is sucked in the first suction step. The tenth discharge step is carried out under the condition in which the opening at the one end of the tube 20 soaks in the second liquid L2. In this case, the second liquid L2 discharged in the tenth discharge step joins the second liquid L2 contained in the second vessel 30, whereby the fourth liquid L4 discharged in the ninth discharge step can separate from the tube 20.

The second liquid L2 discharged in the tenth discharge step may be either a part or the whole of the second liquid L2 mixed in the mixing step.

FIG. 8B illustrates a condition in which a part of the second liquid L2 is discharged after completion of the tenth discharge step. In this condition, the liquid column of the second liquid L2 remains within the tube 20, while the fourth liquid L4 is separated from the tube 20. In the tenth discharge step executed under the condition in which the opening at the one end of the tube 20 soaks in the second liquid L2 contained in the second vessel 30, contact between the fourth liquid L4 and the air is avoided. Moreover, in the tenth discharge step performed under the condition in which the opening at the one end of the tube 20 soaks in the second liquid L2 contained in the second vessel 30, the liquid column of the second liquid L2 within the tube 20 can joined the second liquid L2 contained in the second vessel 30 as illustrated in the figure. Thus, the fourth liquid L4 can be easily separated from the opening at the one end of the tube 20. FIG. 8B shows an example of the fourth liquid L4 which forms a liquid drop after separation.

3.3. Advantage

According to the dispensing method in this embodiment, the first liquid L1 and the third liquid L3 can be securely mixed with each other. More specifically, according to the dispensing method in this embodiment, the liquid drops of the first liquid L1 and the third liquid L3 are combined into a liquid drop of the fourth liquid L4 within the reservoir 22 by the mixing step. In this case, the first liquid L1 and the third liquid L3 can be more easily brought into contact with each other than in such a case where the liquid drops of the first liquid L1 and the third liquid L3 are combined within the second vessel 30 after separately discharged into the second vessel 30. Accordingly, more reliable mixture between the first liquid L1 and the third liquid L3 can be achieved in this embodiment.

According to the dispensing method in this embodiment, the first liquid L1, the third liquid L3, and the fourth liquid L4 are sealed by the second liquid L2 when contained in the first vessel 10 and the third vessel 12, and during the respective suction steps, the mixing step, and the respective discharge steps. Therefore, contact between these liquids L1, L3 and L4 and a gaseous phase can be kept avoided. More specifically, according to the dispensing method in this embodiment, the first liquid L1, the third liquid L3, and the fourth liquid L4 handled under the condition of contact with the second liquid L2 during dispensation are difficult to contact the air or the like. In this case, evaporation of the constituent components of the first liquid L1, the third liquid L3, or the fourth liquid L4 into a gaseous phase, and entrance of other substances such as water through a gaseous phase into the first liquid L1, the third liquid L3, or the fourth liquid L4 can be prevented. Accordingly, variations in the concentrations of the first liquid L1, the third liquid L3, and the fourth liquid L4 decrease, which contributes to accurate dispensation.

According to the dispensing method in this embodiment, the fourth liquid L4 is discharged into the second liquid L2 in the ninth discharge step. In this case, the fourth liquid L4 is difficult to remain within the tube 20 or in the vicinity of the one end of the tube 20 in the ninth discharge step. Accordingly, the fourth liquid L4 can be accurately dispensed into the second vessel 30.

4. Fourth Embodiment

Figure 9:
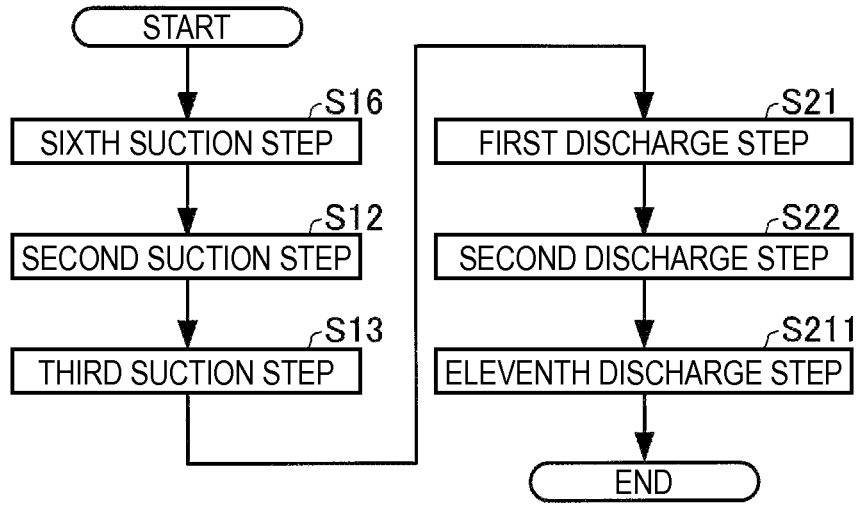
FIG. 9 is a flowchart showing the flow of a dispensing method according to a fourth embodiment.
Figures 10A, 10B, 10C:
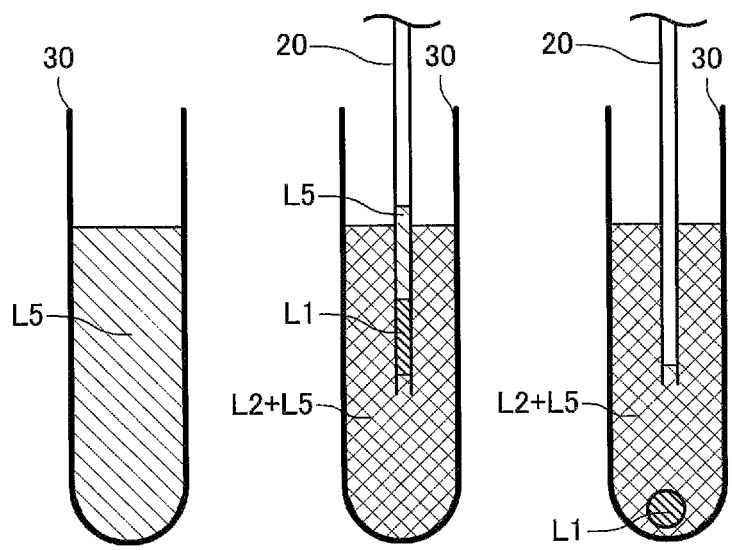
FIG. 10A schematically illustrates a second vessel used in the fourth embodiment.
FIG. 10B schematically illustrates a first discharge step according to the fourth embodiment.
FIG. 10C schematically illustrates a condition after an eleventh discharge step according to the fourth embodiment.

A dispensing method according to a fourth embodiment of the invention is hereinafter described. FIG. 9 is a flowchart showing the flow of the dispensing method in this embodiment. Each of FIGS. 10A through 10C schematically illustrates a part of the steps performed in the dispensing method in this embodiment. FIG. 10A schematically illustrates the second vessel used in this embodiment. FIG. 10B schematically illustrates the first discharge step according to this embodiment. FIG. 10C schematically illustrates a condition after an eleventh discharge step in this embodiment.

4.1. Structure

The dispensing method in this embodiment is a method for dispensing the first liquid L1 contained in the first vessel 10 which stores the first liquid L1 and the second liquid L2 to introduce this first liquid L1 into the second vessel 30 which stores a fifth liquid L5 by using the tube 20.

The first liquid L1, the second liquid L2, the first vessel 10, and the tube 20 in this embodiment are similar to the corresponding liquids and components used in the first embodiment or the second embodiment. Thus, these liquids and components in this embodiment have been given similar reference numbers, and the same explanation is not repeated. According to this embodiment, the fifth liquid L5 is stored in the second vessel 30 beforehand.

4.1.1. Fifth Liquid

The fifth liquid L5 is a liquid not miscible with the first liquid L1. In addition, the fifth liquid L5 is a liquid having lower specific gravity than that of the first liquid L1. The fifth liquid L5 is a liquid, however, which is miscible with the second liquid L2. The fifth liquid L5 may be a liquid of oil-base type when the first liquid L1 is of water-base type similarly to the second liquid L2. For example, when the first liquid L1 is a reaction liquid for PCR, the fifth liquid L5 may be constituted by oil. Examples of oil forming the fifth liquid L5 include oils of the silicon family such as dimethyl silicon oil, oils of the paraffin family, mineral oil, and a mixture of these oils.

4.2. Dispensing Method

The dispensing method in this embodiment includes a sixth suction step, the second suction step, the third suction step, the first discharge step, the second discharge step, and the eleventh discharge step.

The second suction step, the third suction step, the first discharge step, and the second discharge step in this embodiment are similar to the corresponding steps in the first embodiment except that the second suction step is performed after the sixth suction step. Thus, these steps in this embodiment have been given similar reference numbers, and the same explanation is not repeated. FIG. 10A shows a condition in which the fifth liquid L5 is contained in the second vessel 30.

4.2.1. Sixth Suction Step

In the sixth suction step (step S16), the second liquid L2 or the fifth liquid L5 is sucked into the tube 20 through the one end of the tube 20. When the second liquid L2 is sucked in the sixth suction step, the second liquid L2 sucked in this step may be either the second liquid L2 contained in the first vessel 10 or the second liquid L2 stored in another vessel. When the fifth liquid L5 is sucked in the sixth suction step, the fifth liquid L5 sucked in this step may be either the fifth liquid L5 contained in the second vessel 30 or the fifth liquid L5 stored in another vessel. The volume of the second liquid L2 or the fifth liquid L5 sucked in the sixth suction step is not specifically limited. It is preferable that the volume of the second liquid L2 or the fifth liquid L5 is sufficient for eliminating the effect of the gas contained in the tube 20 on the first liquid L1 sucked in the second suction step.

The sixth suction step brings the second liquid L2 or the fifth liquid L5 into contact with the inner wall of the tube 20 so as to prevent easy adhesion of the first liquid L1 sucked in the second suction step to the inner wall of the tube 20, and allow easy shift of the first liquid L1 sucked in the second suction step within the tube 20. The sixth suction step avoids easy contact between the first liquid L1 sucked in the second suction step and the gas contained in the tube 20.

After the sixth suction step, a liquid column of the second liquid L2 is formed at the one end of the tube 20. According to this embodiment, the second suction step (step S12) is performed after the sixth suction step (step S16). Then, similarly to the first embodiment, the third suction step (step S13), the first discharge step (step S21), and the second discharge step (step S22) are executed in this order. After the second discharge step, the liquid column of the second liquid L2 or the fifth liquid L5 remains within the tube 20, and the first liquid L1 comes out of the tube 20 while contacting the one end of the tube 20 (see FIG. 3C).

According to this embodiment, the fifth liquid L5 contained in the second vessel 30 beforehand mixes with the second liquid L2 after the first discharge step. Thus, in the eleventh discharge step, a liquid mixture of the fifth liquid L5 and the second liquid L2 is contained in the second vessel 30.

4.2.2. Eleventh Discharge Step

The eleventh discharge step (step S211) is continuously performed after the second discharge step (step S22). In the eleventh discharge step, at least a part of the second liquid L2 or the fifth liquid L5 sucked into the tube 20 in the sixth suction step (step S16) is discharged into the second vessel 30 through the one end of the tube 20. The one end of the tube 20 through which the second liquid L2 or the fifth liquid L5 is discharged in the eleventh discharge step corresponds to the one end of the tube 20 through which the second liquid L2 or the fifth liquid L5 is sucked in the sixth suction step.

The eleventh discharge step is carried out under the condition in which the opening at the one end of the tube 20 soaks in the mixture of the fifth liquid L5 and the second liquid L2 contained in the second vessel 30. In this case, the second liquid L2 or the fifth liquid L5 discharged in the eleventh discharge step joins the mixture of the fifth liquid L5 and the second liquid L2 contained in the second vessel 30, whereby the first liquid L1 discharged in the second discharge step can separate from the tube 20.

The second liquid L2 or the fifth liquid L5 discharged in the eleventh discharge step may be either a part or the whole of the second liquid L2 or the fifth liquid L5 sucked into the tube 20 in the sixth suction step.

FIG. 10C illustrates a condition in which a part of the fifth liquid L5 is discharged after completion of the eleventh discharge step. In this condition, the liquid column of the fifth liquid L5 remains within the tube 20, while the first liquid L1 is separated from the tube 20. In the eleventh discharge step performed under the condition in which the opening at the one end of the tube 20 soaks in the mixture of the fifth liquid L5 and the second liquid L2 contained in the second vessel 30, the first liquid L1 is difficult to contact the air. Moreover, in the eleventh discharge step performed under the condition in which the opening at the one end of the tube 20 soaks in the mixture of the fifth liquid L5 and the second liquid L2 contained in the second vessel 30, the liquid column of the fifth liquid L5 within the tube 20 can be combined with the mixture of the fifth liquid L5 and the second liquid L2 contained in the second vessel 30 as illustrated in the figure. Accordingly, the first liquid L1 can easily separate from the opening at the one end of the tube 20. FIG. 10C shows an example of the first liquid L1 forming a liquid drop after separation.

4.3. Advantages

According to the dispensing method in this embodiment, the first liquid L1 contained in the first vessel 10, and during the respective suction steps and discharge steps is sealed by the second liquid L2 or the fifth liquid L5. Therefore, contact between the first liquid L1 and a gaseous phase (such as air) is avoided. More specifically, according to the dispensing method in this embodiment, the first liquid L1 handled in the condition of contact with the second liquid L2 or the fifth liquid L5 during dispensation from the first vessel 10 into the second vessel 30 is difficult to contact the air or the like. In this case, evaporation of the constituent components of the first liquid L1 into a gaseous phase, and entrance of other substances such as water through a gaseous phase into the first liquid L1 can be prevented. Accordingly, variations in the concentrations of the solvent and solutes of the first liquid L1 decrease, which contributes to accurate dispensation. According to the dispensing method in this embodiment, the first liquid L1 is discharged into the mixture of the fifth liquid L5 and the second liquid L2 in the second discharge step. In this case, the first liquid L1 is difficult to remain within the tube 20 or in the vicinity of the one end of the tube 20 in the second discharge step. Accordingly, the first liquid L1 contained in the first vessel 10 can be accurately dispensed into the second vessel 30.

5. Other Examples

According to the respective embodiments explained herein, at least either the second liquid L2 or the fifth liquid L5 may have conductivity.

For making the second liquid L2 or the fifth liquid L5 conductive, an additive such as carbinol denatured oil, and a mixture of trimethylsiloxysilicate and cyclopentasiloxane may be added to the second liquid L2 or the fifth liquid L5, for example. A preferable amount of the additive is determined such that the electrical resistivity of the second liquid L2 or the fifth liquid L5 becomes 1012 [Ω·m] or lower. In this case, the proportion of the additive given within this range corresponds to 3% or lower.

When at least either the second liquid L2 or the fifth liquid L5 has conductivity, the first liquid L1, the third liquid L3, the fourth liquid L4, the tube 20, the first vessel 10, the third vessel 12, and the second vessel 30 are not easily charged. Thus, the dispensation can be further stabilized.

Particularly, when liquid of a volume in nanoliters is handled in the respective embodiments, the possibility of various problems increases during dispensation performed under the condition in which at least either the second liquid L2 or the fifth liquid L5 is charged. Examples of these problems include difficult separation of the liquids from the tube 20 and easy flow of the liquids out of the vessels at the time of suction and discharge during the respective steps and at the time of movement of the tube 20. However, when at least either the second liquid L2 or the fifth liquid L5 is conductive, these problems can be reduced.

In the fourth embodiment, conductivity given to the fifth liquid L5 can prevent an unexpected action of either the first liquid L1 or the second liquid L2 when at least either the first liquid L1 or the second liquid L2 is charged, which action may be caused by the electrostatic attractive force or repulsive force produced between the fifth liquid L5 and the charged first liquid L1 or second liquid L2 in the vicinity of the tip of the tube 20 during the respective discharge steps. Accordingly, the first liquid L1 contained in the first vessel 10 can be more securely dispensed into the second vessel 30.

In the first embodiment through fourth embodiment, conductivity given to the second liquid L2 can prevent an unexpected action of at least the first liquid L1 when the respective liquids are charged, which action may be caused by the electrostatic attractive force or repulsive force produced between the first liquid L1 and the second vessel 30 or substances contained in the second vessel 30 in the vicinity of the tip of the tube 20 during the respective discharge steps. Accordingly, the first liquid L1 can be more securely dispensed into the second vessel 30.

It should be easily understood that a part or the whole of the dispensing method according to the embodiments, modified example, and other examples of the invention can be combined for practicing the dispensing method of the invention.

6. Dispensing Device

Figure 11:
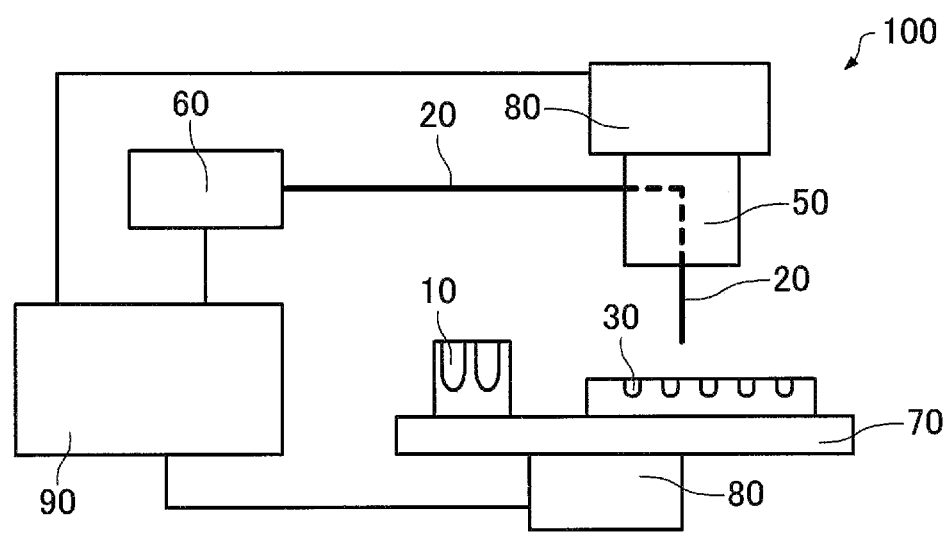
FIG. 11 schematically illustrates an example of a dispensing device.

The dispensing method according to the respective embodiments may be performed by either an operator or a dispensing device discussed hereinafter. A dispensing device 100 shown herein is an example of the dispensing device capable of performing the dispensing method of the embodiments. FIG. 11 schematically illustrates the structure of the dispensing device 100. The dispensing device 100 includes the tube 20, a support member 50, a pump 60, a stage 70, a shifting mechanism 80, and a controller 90.

The tube 20 which corresponds to the tube 20 described in the respective embodiments is supported by the support member 50 such that the one end of the tube 20 projects downward from the support member 50. The other end of the tube 20 is connected with the pump 60.

The support member 50 is a component for supporting the tube 20. The support member 50 may have a mechanism associated with replacement of the tube 20. The support member 50 can be shifted by the shifting mechanism 80.

The pump 60 can suck the interior of the tube 20 from the other end of the tube 20, and apply pressure to the interior of the tube 20 from the other end of the tube 20. The suction and pressurization performed by the pump 60 can be controlled by the controller 90.

The stage 70 is a unit on which the vessels or the like can be placed. According to the example shown in FIG. 11, the first vessel 10 and the second vessel 30 are placed on the stage 70. The stage 70 can be shifted by the shifting mechanism 80. The shifting mechanism 80 is a mechanism capable of changing the relative positions of the support member 50 and the stage 70. According to the example shown in the figure, the shifting mechanism 80 is provided for each of the support member 50 and the stage 70. However, the shifting mechanism 80 may be equipped on either of these components. The shifting mechanism 80 can shift the tube 20 between the respective vessels by changing the relative positions of the support member 50 and the stage 70, and vary the position of the one end of the tube 20 within the respective vessels.

The controller 90 can control the operations of the pump 60 and the shifting mechanism 80. The controller 90 may be constituted by an electronic calculator (such as a personal computer), for example. The controller 90 may include a program for controlling the operations of the pump 60 and the shifting mechanism 80 in conformity with the dispensing method described herein. The dispensing device 100 having this structure can perform the dispensing method shown in the respective embodiments, and therefore can carry out dispensation of the first liquid L1 contained in the first vessel 10 into the second vessel 30, for example.

The invention is not limited to the embodiments described and depicted herein, but may be practiced otherwise in various ways. For example, a structure substantially equivalent to the structure explained in the embodiments (such as a structure associated with an equivalent function, method, or result, and a structure achieving an equivalent object or advantage); a structure which contains parts not essential and different from the corresponding parts in the embodiments in place of these parts; a structure which can offer an advantage equivalent to the corresponding advantage in the embodiments or achieve an object equivalent to the corresponding object in the embodiments; and a structure as a combination of the structure described in the embodiments and a known technology are all included in the scope of the invention.

What is claimed is:

1. A dispensing device, comprising:
a first vessel, storing a first liquid and a second liquid, the second liquid being immiscible with the first liquid and having a lower specific gravity than the first liquid;
a second vessel, storing the second liquid;
a tube;
a pump; and
a controller, which controls a suction and pressurization performed by the pump, wherein the controller is programmed to:
suck the second liquid contained in the first vessel into the tube through one end of the tube,
suck the first liquid contained in the first vessel into the tube through the one end of the tube so that the tube has the first liquid and the second liquid,
suck the second liquid contained in the first vessel into the tube through the one end of the tube so that in the tube, the first liquid is sandwiched by the second liquid,
discharge the second liquid which has been sucked into the tube into the second vessel in which the second liquid already exists,
discharge the first liquid which has been sucked into the tube into the second liquid contained in the second vessel, and
discharge at least a part of the second liquid which has sucked into the tube into the second vessel.

2. A dispensing device, comprising:
a first vessel, storing a first liquid and a second liquid, the second liquid being immiscible with the first liquid and having a lower specific gravity than the first liquid;
a second vessel, storing the second liquid;
a third vessel, storing the second liquid and a third liquid, the third liquid being immiscible with the second liquid and having a larger specific gravity than the second liquid;
a tube;
a pump; and
a controller, which controls a suction and pressurization performed by the pump, wherein the controller is programmed to:
suck the second liquid contained in the first vessel into a tube through one end of the tube,
suck the first liquid contained in the first vessel into the tube through the one end of the tube so that the tube has the first liquid and the second liquid,
suck the second liquid contained in the first vessel into the tube through the one end of the tube so that in the tube, the first liquid is sandwiched by the second liquid, suck the third liquid contained in the third vessel into the tube through the one end of the tube so that the tube has the first liquid, the second liquid and the third liquid,
suck the second liquid contained in the third vessel into the tube through the one end of the tube so that in the tube, the first liquid and the third liquid are respectively sandwiched by the second liquid,
discharge the second liquid which has been sucked into the tube into the second vessel in which the second liquid already exists,
discharge the third liquid which has been sucked into the tube into the second vessel,
discharge a part of the second liquid which has been sucked into the tube into the second vessel,
discharge the second liquid remaining within the tube into the second vessel, discharge the first liquid which has been sucked into the tube into the second vessel, and
discharge at least a part of the second liquid which has been sucked into the tube into the second vessel.

3. A dispensing device, comprising:
a first vessel, storing a first liquid and a second liquid, the second liquid being immiscible with the first liquid and having a lower specific gravity than the first liquid;
a second vessel, storing the second liquid;
a third vessel, storing the second liquid and a third liquid, the third liquid being immiscible with the second liquid and having a larger specific gravity than the second liquid;
a reservoir;
a tube with one end is open and the other end is connected with the reservoir;
a pump; and
a controller, which controls a suction and pressurization performed by the pump, wherein the controller is programmed to:
suck the second liquid contained in the first vessel into the tube through the one end of the tube,
suck the first liquid contained in the first vessel into the tube through the one end of the tube so that the tube has the first liquid and the second liquid,
suck the second liquid contained in the first vessel into the tube through the one end of the tube so that in the tube, the first liquid is sandwiched by the second liquid, suck the third liquid contained in the third vessel into the tube through the one end of the tube so that the tube has the first liquid, the second liquid and the third liquid, suck the second liquid contained in the third vessel into the tube through the one end of the tube so that in the tube, the first liquid and the third liquid are respectively sandwiched by the second liquid, move at least the first liquid and the third liquid into the reservoir such that the first liquid and the third liquid mixes into a fourth liquid, discharge the second liquid remaining within the tube into the second vessel in which the second liquid already exists, discharge the fourth liquid into the second vessel, and discharge at least a part of the second liquid into the second vessel.

4. A dispensing device, comprising:

a first vessel, storing a first liquid and a second liquid, the second liquid being immiscible with the first liquid and having a lower specific gravity than the first liquid;

a second vessel, storing a third liquid, the third liquid being immiscible with the first liquid and being miscible with the second liquid;

a tube;

a pump; and a controller, which controls a suction and pressurization performed by the pump, wherein the controller is programmed to:

suck one of the second liquid contained in the first vessel and the third liquid contained in the second vessel into a tube through one end of the tube, suck the first liquid contained in the first vessel into the tube through the one end of the tube so that the tube has the first liquid and the one of the second liquid and the third liquid, suck the second liquid contained in the first vessel into the tube through the one end of the tube so that in the tube, the first liquid is sandwiched by the second liquid and the one of the second liquid and the third liquid, discharge the second liquid which has been sucked into the tube into the second vessel in which the third liquid already exists, discharge the first liquid which has been sucked into the tube into the second vessel, and discharge at least a part of the one of the second liquid and the third liquid which has been sucked into the tube into the second vessel.

5. The dispensing device according to claim 1, wherein at least the inner wall of the tube has hydrophobic properties.

6. The dispensing device according to claim 2, wherein at least the inner wall of the tube has hydrophobic properties.

7. The dispensing device according to claim 3, wherein at least the inner wall of the tube has hydrophobic properties.

8. The dispensing device according to claim 4, wherein at least the inner wall of the tube has hydrophobic properties.

9. The dispensing device according to claim 4, wherein the third liquid is conductive.

\* \* \* \* \*